US009248176B2

(12) United States Patent
Ficht et al.

(10) Patent No.: US 9,248,176 B2
(45) Date of Patent: Feb. 2, 2016

(54) **CONTROLLED RELEASE VACCINES AND METHODS FOR TREATING *BRUCELLA* DISEASES AND DISORDERS**

(75) Inventors: Thomas A. Ficht, College Station, TX (US); Allison R. Ficht, College Station, TX (US); Renee Tsolis, Davis, CA (US); Leslie Garry Adams, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 732 days.

(21) Appl. No.: 13/269,382

(22) Filed: Oct. 7, 2011

(65) Prior Publication Data

US 2014/0248354 A1 Sep. 4, 2014

Related U.S. Application Data

(60) Provisional application No. 61/390,705, filed on Oct. 7, 2010.

(51) Int. Cl.
*A61K 39/02* (2006.01)
*A61K 39/00* (2006.01)

(52) U.S. Cl.
CPC ......... *A61K 39/098* (2013.01); *A61K 2039/522* (2013.01); *A61K 2039/622* (2013.01)

(58) Field of Classification Search
CPC . A61K 38/17; A61K 2300/00; A61K 39/003; A61K 39/98; A61K 38/00
USPC ........................................... 424/252.1, 234.1
See application file for complete search history.

(56) References Cited

U.S. PATENT DOCUMENTS

| | | | | |
|---|---|---|---|---|
| 3,515,708 | A * | 6/1970 | Williams | 424/252.1 |
| 4,389,330 | A * | 6/1983 | Tice et al. | 427/213.36 |
| 4,732,763 | A * | 3/1988 | Beck et al. | 424/433 |
| 5,192,566 | A * | 3/1993 | Cox et al. | 428/89 |
| 5,939,075 | A * | 8/1999 | Houng et al. | 424/252.1 |

(Continued)

FOREIGN PATENT DOCUMENTS

WO 2007/120309 * 10/2007 ............... C12N 1/00

OTHER PUBLICATIONS

Arenas-Gamboa, AM et al, Infection and Immunity, vol. 77(2), pp. 877-884, Feb. 2009, The *Brucella abortus* S19 Delta-vjbR live Vaccine Candidate is safer than S19 and confers protection against wild type Challegne in Balb/c Mice when Delivered in a sustained-release vehicle.*

(Continued)

*Primary Examiner* — Albert Navarro
*Assistant Examiner* — Ginny Portner
(74) *Attorney, Agent, or Firm* — Edwin S. Flores; Daniel J. Chalker; Chalker Flores, LLP

(57) ABSTRACT

Methods and compositions for the treatment of *Brucella* induced diseases and disorders are disclosed herein. In preferred embodiments, the invention relates to vaccines. In additional embodiments, the invention relates to formulations capable of releasing said vaccines at a controlled rate of release in vivo. In further embodiments, the invention relates to modified strains of the bacteria *Brucella melitensis* and *Brucella abortus*. In still further embodiments, the invention relates to compositions that do not induce clinical symptoms or splenomegaly in a subject receiving said compositions.

24 Claims, 10 Drawing Sheets

(56) References Cited

U.S. PATENT DOCUMENTS

| | | | | |
|---|---|---|---|---|
| 6,264,991 | B1 * | 7/2001 | Barrow et al. | 424/501 |
| 7,364,745 | B2 * | 4/2008 | Bandara et al. | 424/252.1 |
| 7,416,878 | B2 * | 8/2008 | Nikolich et al. | 435/252.3 |
| 7,541,447 | B2 | 6/2009 | Ugalde et al. | |
| 8,075,879 | B2 * | 12/2011 | Rajashekara et al. | 424/93.2 |
| 8,778,655 | B2 * | 7/2014 | Gorvel et al. | 435/252.3 |
| 2001/0014673 | A1 * | 8/2001 | Nikolich et al. | 514/100 |
| 2004/0224030 | A1 * | 11/2004 | Shastri et al. | 424/490 |
| 2005/0142151 | A1 * | 6/2005 | Nikolich et al. | 424/252.1 |
| 2005/0249755 | A1 * | 11/2005 | Nikolich et al. | 424/252.1 |
| 2005/0260258 | A1 * | 11/2005 | Ficht et al. | 424/450 |
| 2006/0093621 | A1 * | 5/2006 | Bandara et al. | 424/200.1 |
| 2006/0153868 | A1 * | 7/2006 | Ugalde et al. | 424/200.1 |
| 2007/0036823 | A1 * | 2/2007 | Bandara et al. | 424/200.1 |
| 2011/0177127 | A1 | 7/2011 | Andrews et al. | |
| 2012/0093773 | A1 * | 4/2012 | Li et al. | 424/93.2 |
| 2012/0183576 | A1 * | 7/2012 | Gorvel et al. | 424/252.1 |
| 2014/0286996 | A1 * | 9/2014 | Gorvel et al. | 424/234.1 |

OTHER PUBLICATIONS

Crasta, Oswald R. et al, PLOS one, May 2008, vol. 3(5), e2193, pp. 1-13, Genome Sequence of *Brucella abortus* Vaccine Strain S19 Compared to Viruent Strains yields Candidate Virulence Genes.*

Arenas-Gamboa, Angela M et al, Infection and Immunity, Jun. 2008, pp. 2448-2455, vol. 76(6), Immunization with a single dose of a microencapsulated *Brucella melitensis* Mutant Enhances Protection against Wild-Type Challenge.*

Rolan, HG et al, Clinical and Vaccine Immunology, vol. 15(2), pp. 208-212, Feb. 2008, VirB is a Serological Marker of *Brucella* Infection in Experimental and Natural hosts.* den Hartigh, Andreas B et al, Infection and Immunity, Sep. 2004, vol. 72(9), pp. 5143-5149, Differential Requirements for VirB1 and VirB2 during *Brucella abortus* Infection.*

Delrue, Rose-May et al, Cellular Microbiology, 2005, vol. 7(8), pp. 1151-1161, A quorum sensing regulator controls expredssion of both the type IV secretion system and the flagellar apparatus of *Brucella melitensis*.*

Allen, Chris A., et al., "Transposon-Derived *Brucella* abortusRough Mutants Are Attenuated and Exhibit Reduced Intracellular Survival," Infection and Immunity 1988, 66:1008-1016.

Arenas-Gamboa, A. M., et al., "The *Brucella abortus* S19 DeltavjbR Live Vaccine Candidate is Safer than S19 and Confers Protection against Wild-Type Challenge in BALB/c Mice When Delivered in a Sustained-Release Vehicle," Infection and Immunity, Feb. 2009, 77:877-884.

Bahlawane, Christelle, et al., "Fine-Tuning of Galactoglucan Biosynthesis in Sinorhizobium meliloti by Differential WggR (ExpG)-, PhoB-, and MucR-Dependent Regulation of Two Promoters," Journal of Bacteriology, May 2008, 190:3456-3466.

Bahlawane, Christelle, et al., "Sinorhizobium meliloti Regulator MucR Couples Exopolysaccharide Synthesis and Motility," Mol Plant Microbe Interact, 2008, 21:1498-1509.

Bossi, P., et al., "Bichat guidelines for the clinical management of brucellosis and bioterrorism-related brucellosis," Euro Surveill, 2004, 9:E15-16.

Cassataro, Julia, et al. "A DNA Vaccine Coding for the *Brucella* Outer Membrane Protein 31 Confers Protection against *B. melitensis* and *B. ovis* Infection by Eliciting a Specific Cytotoxic Response," Infection and Immunity 2005, 73(10):6537-6546.

Cespedes, Sandra, et al., "Identification and partial characterisation of a new protective antigen of *Brucella abortus*," Journal of Medical Microbiology (2000) 49:165-170.

Costerton, J. William, et al., "Overview of microbial biofilms," Journal of Industrial Microbiology (1995), 15:137-140.

Costerton, J. William, et al., "Microbial Biofilms," Annual Review of Microbiology, 1995, 49:711-745.

Ficht, Thomas A., et al., "Brucellosis: The Case for Live, Attenuated Vaccines," Vaccine, Nov. 2009, 27(Suppl 4):D40-43.

Hay, Iain, D., et al., "MucR, a Novel Membrane-Associated Regulator of Alginate Biosynthesis in Pseudomonas aeruginosa," Applied and Environmental Microbiology, 2009, 75(4):1110-1120.

Hong, Priscilla C., et al., "Identification of Genes Required for Chronic Persistence of *Brucella abortus* in Mice," Infection and Immunity, 2000, 68(7):4102-4107.

Kahl-McDonagh, M. M., et al., "Aerosol infection of BALB/c Mice with *Brucella melitensis* and *Brucella abortus* and Protective Efficacy against Aerosol Challenge," Infection and Immunity, Oct. 2007, vol. 75, No. 10, pp. 4923-4932.

Kahl-McDonagh, M. M., et al., "Evaluation of Protection Afforded by *Brucella abortus* and *Brucella melitensis* Unmarked Deletion Mutants Exhibiting Different Rates of Clearance in BALB/c Mice," Infection and Immunity, Jul. 2006, 74:4048-4057.

Montaraz, J. A., et al., "Comparison of living and nonliving vaccines for *Brucella abortus* in BALB/c mice," Infection and Immunity, 1986, 53(2):245-251.

Mueller, Konrad, : et al "Complex Regulation of Symbiotic Functions is Coordinated by MucR and Quorum Sensing in Sinorhizobium meliloti," Journal of Bacteriology, Nov. 5, 2010, 193(2):485-496.

Onate, Angel A., et al., "A DNA Vaccine Encoding Cu,Zn Superoxide Dismutase of *Brucella abortus* Induces Protective Immunity in BALB/c Mice," Infection and Immunity, Sep. 2003, 71:4857-4861.

Pasquevich, Karina A., et al., "Immunization with Recombinant *Brucella* Species Outer Membrane Protein Omp16 or Omp19 in Adjuvant Induces Specific CD4+ and CD8+ T Cells as Well as Systemic and Oral Protection against *Brucella abortus* Infection," Infection and Immunity, Jan. 2009, 77:436-445.

Spink, Wesley W., et al., "Immunization with Viable *Brucella* Organisms—Results of a Safety Test in Humans," Bull World Health Organization, 1962, 26:409-419.

Wu, Qingmin, et al., "Mariner mutagenesis of *Brucella melitensis* reveals genes with previously uncharacterized roles in virulence and survival," BMC Microbiology, Dec. 18, 2006, 6:102.

* cited by examiner

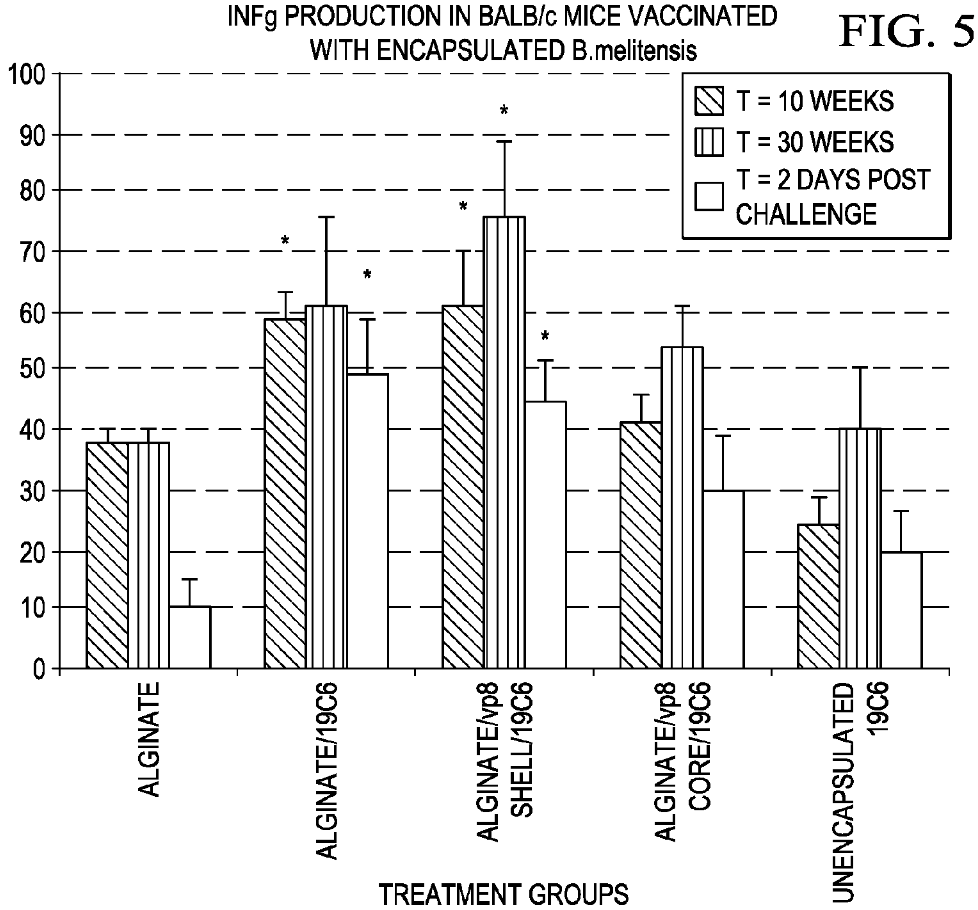

FIG. 5

INFg PRODUCTION IN BALB/c MICE VACCINATED WITH ENCAPSULATED B.melitensis

Legend:
- T = 10 WEEKS
- T = 30 WEEKS
- T = 2 DAYS POST CHALLENGE

Treatment groups: ALGINATE, ALGINATE/19C6, ALGINATE/vp8 SHELL/19C6, ALGINATE/vp8 CORE/19C6, UNENCAPSULATED 19C6

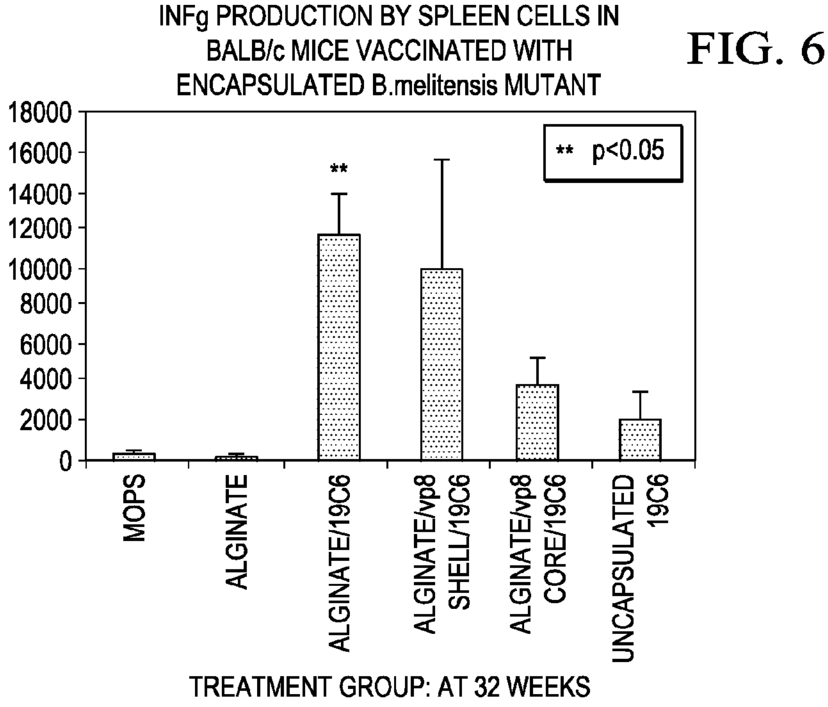

FIG. 6

INFg PRODUCTION BY SPLEEN CELLS IN BALB/c MICE VACCINATED WITH ENCAPSULATED B.melitensis MUTANT

** $p < 0.05$

TREATMENT GROUP: AT 32 WEEKS

Treatment groups: MOPS, ALGINATE, ALGINATE/19C6, ALGINATE/vp8 SHELL/19C6, ALGINATE/vp8 CORE/19C6, UNCAPSULATED 19C6

CONTROLLED RELEASE VACCINES AND METHODS FOR TREATING *BRUCELLA* DISEASES AND DISORDERS

CROSS-REFERENCE TO RELATED APPLICATIONS

This application is a non-provisional application of U.S. Provisional Patent Application No. 61/390,705 filed on Oct. 7, 2010 and entitled "Controlled Release Vaccines and Methods of Treating *Brucella* Diseases and Disorders" the entire contents of which is incorporated herein by reference.

STATEMENT OF FEDERALLY FUNDED RESEARCH

This invention was made with U.S. Government support under Contract No. W81XWH-07-1-0304 from the Department of Defense (DOD), US Army Medical Research and Material Command, Contract Nos. 1U54A1057156-0100, R41 AI068252-01A2, and T32-0200016, from the National Institutes of Health (NIH), and Contract Nos. 99-35204-7550 and 2002-38420-5806, from the United State Department of Agriculture. The government has certain rights in this invention.

TECHNICAL FIELD OF THE INVENTION

The present invention relates in general to methods and compositions for the treatment of *Brucella* induced diseases and disorders. In preferred embodiments, the invention relates to vaccines. In additional embodiments, the invention relates to formulations capable of releasing said live vaccines at a controlled rate of release in vivo. In further embodiments, the invention relates to modified strains of the bacteria *Brucella melitensis*, and *Brucella abortus* either to reduce virulence or to provide a diagnostic marker. In still further embodiments, the invention relates to compositions that do not induce clinical symptoms or splenomegaly in a subject receiving said compositions.

REFERENCE TO A SEQUENCE LISTING

The present application includes a Sequence Listing filed separately as required by 37 CFR 1.821-1.825.

BACKGROUND OF THE INVENTION

Without limiting the scope of the invention, its background is described in connection with controlled release vaccines and use of *Brucella* strains in vaccine manufacturing.

Andrews and Lowry have described compositions and methods for the diagnosis and prevention of *B. abortus* infection in U.S. Patent Application Publication No. 2011/0177127. The invention describes a method of detecting a *Brucella abortus* infection in an animal, comprising the steps of: a) obtaining a biological sample from said animal; and b) detecting the presence of at least one antibody immunologically specific for at least one *Brucella abortus* protein, wherein the presence of antibodies to the *Brucella abortus* protein indicates a *Brucella abortus* infection in said animal.

At present, no human brucellosis vaccine is available even though *Brucella* species are isolated from 86 countries, with 500,000 new cases of brucellosis appearing each year throughout Latin America, the Mediterranean littoral, Arabian peninsula, Africa, central Asia and the Far East (WHO, 2006); as a result, prevention of human brucellosis has focused upon the reduction in animal disease. The animal vaccine strains employed today are fortuitous isolates attenuated in ability to cause abortion due to reduced replication in reproductive tissues. The attenuation of these mutants does not extend to reticuloendothelial disease observed in mice and in humans, except in the case of the rough strain RB51. The lack of genetic definition of fortuitous isolates limits the usefulness of vaccine strains, preventing complete description of their stability, and warrants caution when applied to human use as disclosed in Sangari et al (1998) *Vaccine* 16, 1640-5 and Schurig et al (1991) *Vet. Microbiol.* 28, 171-88. Of the currently available vaccine strains, only *B. abortus* S19 and *B. melitensis* Rev 1 have been tested in humans as provided for in Spink et al. *Bull World Health Organ* (1962) 26, 409-19 and Spink & Thompson (1953) *JAMA* 153, 1162-1165, which are hereby incorporated by reference. Revl was found to be highly unsuitable with ⅔ of the "volunteers" exhibiting symptoms of disease and colonization by the organism. However, a subculture of S19 referred to as 19-BA provided results that are more palatable. Only two volunteers (12%) exhibited symptoms of disease, and the organism was isolated from one of these volunteers. 19-BA was originally used to vaccinate at least 3 million people in the Soviet Union as described in Vershilova Bull World Health Organ (1961) 24, 85-9. These investigators concluded that there were more problems due to hypersensitivity than to persistence of the organism. Eight percent complained of headache and malaise, and 2% showed signs of febrile illness. Clearly, a vaccine with this much side effect would not be and should not be tolerated given our current state of knowledge. Given the potential threat this organism poses, there is a need to develop a better human vaccine.

One such example of a live vaccine against brucellosis is described in U.S. Pat. No. 7,541,447 issued to Ugalde et al. (2009). The Ugalde invention comprises a live vaccine for immunization, prophylaxis or treatment of brucellosis comprising a bacterium modified by partial or complete deletion of the pgm gene, rendering the bacterium incapable of synthesizing a key enzyme in the metabolism of bacterial sugars. The vaccine of the '447 patent discloses nucleotide sequence fragments having the aforementioned deletion and is either lyophilized or is in a pharmaceutical vehicle.

SUMMARY OF THE INVENTION

The present invention relates to methods and compositions for the treatment of *Brucella* induced diseases and disorders. In preferred embodiments, the invention relates to vaccines. In additional embodiments, the invention relates to formulations capable of releasing said live vaccines at a controlled rate of release in vivo. In further embodiments, the invention relates to modified strains of the bacteria *Brucella melitensis*, and *Brucella abortus* either to reduce virulence or to provide a diagnostic marker. In still further embodiments, the invention relates to compositions that do not induce clinical symptoms and splenomegaly in a subject receiving said compositions.

The present invention in one embodiment discloses a vaccine composition comprising: (i) a *Brucella* strain comprising one or more attenuating gene knockouts and further comprising a diagnostic gene knockout and (ii) an encapsulating agent comprising vitelline protein B capable of releasing the *Brucella* strain at a predetermined rate. In one aspect the composition disclosed hereinabove comprises an optional adjuvant or a pharmaceutically acceptable carrier. In another aspect the encapsulating agent is an alginate bead or a microsphere. In yet another aspect the *Brucella* strain is selected from the group consisting of *Brucella melitensis* and *Brucella abortus*. In a related aspect the *Brucella abortus* is a *Brucella abortus* S19 strain.

In another aspect the attenuating gene knockout is selected from the group consisting of ΔvjbR, ΔmucR, ΔmanB/A, Δasp24, ΔvirB1, ΔvirB2, ΔvirB3, ΔvirB4, ΔvirB5, ΔvirB6, ΔvirB7, ΔvirB8, ΔvirB9, ΔvirB10, and ΔvirB11. In another aspect said diagnostic gene knockout comprises a differentiation of infected animals from vaccinated animals (DIVA) mutant that includes ΔvirB12, Δbcsp31, and Δasp24. In yet another aspect the attenuating gene knockout comprises ΔvjbR, ΔmucR, ΔvirB2, or ΔmanB/A. In one aspect the vaccine further comprises a marker for serological testing, wherein the marker is DIVA mutant comprising ΔvirB12, Δbcsp31, Δasp24, or any combinations thereof. In another aspect the vaccine comprises ΔmucR/DIVA, ΔvjbR/DIVA, ΔvirB2/DIVA, ΔmanB/A/DIVA, or any combinations thereof. In yet another aspect the strain is a double mutant and further comprises a third mutation, wherein the third mutation is a marker for serological testing. In a specific aspect the double mutant is selected from the group consisting of a ΔvirB2/ΔmanB/A mutant, ΔvjbR/ΔmucR mutant, ΔvirB2/ΔmucR mutant, ΔvirB2/ΔvjbR mutant, ΔvjbR/ΔmanB/A mutant, and ΔmucR/ΔmanB/A mutant. In one aspect the third mutation is DIVA mutant comprising ΔvirB12, Δbcsp31, Δasp24, or any combinations thereof. In another aspect the strain comprises ΔvjbR/ΔmucR/DIVA mutant, ΔvirB2/ΔmanB/A/DIVA mutant, ΔvirB2/ΔvjbR/DIVA mutant, ΔvirB2/ΔmucR/DIVA mutant, ΔvjbR/ΔmanB/A/DIVA mutant, and ΔmucR/ΔmanB/A/DIVA mutant.

In yet another aspect the composition described hereinabove further comprises one or more optional antibiotic markers, wherein the antibiotic marker is Kanamycin. In one aspect the vaccine is used for a prophylaxis, an amelioration of symptoms, a treatment, or any combinations thereof against brucellosis in a human or an animal subject. In another aspect the vaccine is administered by an oral, an intranasal, a parenteral, an intradermal, an intramuscular, an intraperitoneal, an intravenous, a subcutaneous, an epidural, a mucosal, a rectal, a vaginal, a sublingual, or a buccal route.

Another embodiment of the instant invention relates to a vaccine composition comprising: a single or a double mutant strain of *Brucella* comprising one or more attenuating gene knockouts and further comprising a diagnostic gene knockout, wherein the attenuating gene knockouts comprise ΔmucR, ΔvjbR, ΔmanB/A, ΔvirB2, ΔvirB2/ΔmanB/A mutant, ΔvjbR/ΔmucR mutant, ΔvirB2/ΔmucR mutant, ΔvirB2/ΔvjbR mutant, ΔvjbR/ΔmanB/A mutant, ΔmucR/ΔmanB/A mutant, or any combinations thereof, wherein the diagnostic gene knockout comprises a differentiation of infected animals from vaccinated animals (DIVA) mutant that includes ΔvirB12, Δbcsp31, Δasp24, or any combinations thereof; and an encapsulating agent comprising vitelline protein B capable of releasing the *Brucella* strain at a predetermined rate.

In yet another embodiment the present invention provides a vaccine composition comprising (a) a single or double mutant strain of *Brucella melitensis* and *Brucella abortus* strain comprising: (i) one or more attenuating gene knockouts and further comprising a diagnostic gene knockout, wherein the attenuating gene knockouts comprise ΔmucR, ΔvjbR, ΔmanB/A, ΔvirB2, ΔvirB2/ΔmanB/A mutant, ΔvjbR/ΔmucR mutant, ΔvirB2/ΔmucR mutant, ΔvirB2/ΔvjbR mutant, ΔvjbR/ΔmanB/A mutant, and ΔmucR/ΔmanB/A mutant, or any combinations thereof and (ii) a marker for serological testing, wherein the marker is a differentiation of infected animals from vaccinated animals (DIVA) mutant comprising ΔvirB12, Δbcsp31, Δasp24, or any combinations thereof and, (b) an encapsulating agent comprising vitelline protein B capable of releasing the strain at a predetermined rate.

In yet another embodiment the present invention discloses a method for evaluating efficacy of a vaccine against brucellosis in an animal subject comprising the steps of: i) providing a vaccine comprising: a single or a double mutant strain of *Brucella* comprising one or more attenuating gene knockouts and further comprising a diagnostic gene knockout, wherein the attenuating gene knockouts comprise ΔmucR, ΔvjbR, ΔvirB2, ΔmanB/A, ΔvirB2/ΔmanB/A mutant, ΔvjbR/ΔmucR mutant, ΔvirB2/ΔmucR mutant, ΔvirB2/ΔvjbR mutant, ΔvjbR/ΔmanB/A mutant, ΔmucR/ΔmanB/A mutant, or any combinations thereof, wherein the diagnostic gene knockout comprises a differentiation of infected animals from vaccinated animals (DIVA) mutant that includes ΔvirB12, Δbcsp31, Δasp24, or any combinations thereof; and an encapsulating agent comprising vitelline protein B capable of releasing the *Brucella* strain at a predetermined rate; ii) inoculating the animal subject with the vaccine; iii) providing one or more animal subjects suffering from brucellosis or naturally infected with the *Brucella* strain; iv) performing a DIVA assay based on a diagnostic or serological test to differentiate detection of one or more antibodies against the one or more attenuating gene knockouts in the infected and the vaccinated animal subjects; and v) evaluating efficacy of the vaccine against brucellosis based on a presence or absence of the one or more antibodies against the one or more attenuating gene knockouts. In one aspect of the method the *Brucella* strain is selected from the group consisting of *Brucella melitensis* and *Brucella abortus*, wherein the *Brucella abortus* is a *Brucella abortus* S19 strain.

One embodiment of the present invention relates to a method for prophylaxis, amelioration of symptoms, or any combinations thereof against brucellosis in a human or animal subject comprising the steps of: identifying the human or animal subject in need of the prophylaxis, amelioration of symptoms, or any combinations thereof against brucellosis; and administering a therapeutically effective amount of a vaccine composition to the human or animal subject for the prophylaxis, amelioration of symptoms, or any combinations thereof against brucellosis, wherein the vaccine comprises:

(i) a *Brucella* strain comprising one or more attenuating gene knockouts and further comprising a diagnostic gene knockout;

(ii) an encapsulating agent comprising vitelline protein B capable of releasing the *Brucella* strain at a predetermined rate; and (iii) an optional adjuvant or a pharmaceutically acceptable carrier.

In one aspect of the method hereinabove the *Brucella* strain is selected from the group consisting of *Brucella melitensis* and *Brucella abortus*. More specifically, the *Brucella abortus* is a *Brucella abortus* S19 strain. In another aspect the attenuating gene knockout is selected from the group consisting of ΔvjbR, ΔmucR, ΔmanB/A, Δasp24, ΔvirB1, ΔvirB2, ΔvirB3, ΔvirB4, ΔvirB5, ΔvirB6, ΔvirB7, ΔvirB8, ΔvirB9, ΔvirB10, and ΔvirB11. In another aspect diagnostic gene knockout comprises a differentiation of infected animals from vaccinated animals (DIVA) mutant that includes ΔvirB12, Δbcsp31, and Δasp24. In yet another aspect the attenuating gene knockout comprises ΔvjbR, ΔmucR, ΔvirB2, or ΔmanB/A.

In related aspects the vaccine further comprises a marker for serological testing, wherein the marker is a DIVA mutant comprising ΔvirB12, Δbcsp31, and Δasp24 and comprises ΔmucR/DIVA, ΔvjbR/DIVA, ΔvirB2/DIVA, ΔmanB/A/DIVA, or any combinations thereof. In one aspect the strain is a double mutant and further comprises a third mutation, wherein the third mutation is a marker for serological testing. In another aspect the double mutant is selected from the group consisting of a ΔvirB2/ΔmanB/A mutant, ΔvjbR/ΔmucR mutant, ΔvirB2/ΔmucR mutant, ΔvirB2/ΔvjbR mutant, ΔvjbR/ΔmanB/A mutant, and ΔmucR/ΔmanB/A mutant. In a specific aspect the third mutation is a DIVA mutant. In another aspect the strain comprises ΔvjbR/ΔmucR/DIVA mutant, ΔvirB2/ΔmanB/A/DIVA mutant, ΔvirB2/ΔvjbR/DIVA mutant, ΔvirB2/ΔmucR/DIVA mutant, ΔvjbR/ΔmanB/A/DIVA mutant, and ΔmucR/ΔmanB/A/DIVA mutant.

In yet another aspect the vaccine further comprises one or more optional antibiotic markers, wherein the antibiotic marker is Kanamycin. In one aspect the vaccine is administered by an oral, an intranasal, a parenteral, an intradermal, an intramuscular, an intraperitoneal, an intravenous, a subcutaneous, an epidural, a mucosal, a rectal, a vaginal, a sublingual, or a buccal route.

Another embodiment disclosed herein describes a method for prophylaxis, amelioration of symptoms, or any combinations thereof against brucellosis in a human or animal subject comprising the steps of: a) identifying the human or animal subject in need of the prophylaxis, amelioration of symptoms, or any combinations thereof against brucellosis and b) administering a therapeutically effective amount of a vaccine composition to the human or animal subject for the prophylaxis, amelioration of symptoms, or any combinations thereof against brucellosis, wherein the vaccine comprises:

(i) a single or a double mutant strain of *Brucella* comprising one or more attenuating gene knockouts and further comprising a diagnostic gene knockout, wherein the attenuating gene knockouts comprise ΔmucR, ΔvjbR, ΔmanB/A, ΔvirB2, ΔvirB2/ΔmanB/A mutant, ΔvjbR/ΔmucR mutant, ΔvirB2/ΔmucR mutant, ΔvirB2/ΔvjbR mutant, ΔvjbR/ΔmanB/A mutant, ΔmucR/ΔmanB/A mutant, or any combinations thereof, wherein the diagnostic gene knockout comprises a differentiation of infected animals from vaccinated animals (DIVA) mutant that includes ΔvirB12, Δbcsp31, Δasp24, or any combinations thereof;
(ii) an encapsulating agent comprising vitelline protein B capable of releasing the *Brucella* strain at a predetermined rate; and
(iii) an optional adjuvant or a pharmaceutically acceptable carrier.

In yet another embodiment the present invention provides a method for prophylaxis, amelioration of symptoms, or any combinations thereof against brucellosis in a human or animal subject comprising the steps of: a) identifying the human or animal subject in need of the prophylaxis, amelioration of symptoms, or any combinations thereof against brucellosis and b) administering a therapeutically effective amount of a vaccine composition to the human or animal subject for the prophylaxis, amelioration of symptoms, or any combinations thereof against brucellosis, wherein the vaccine comprises:

(i) a single or double mutant strain of *Brucella melitensis* and *Brucella abortus* strain comprising: one or more attenuating gene knockouts and further comprising a diagnostic gene knockout, wherein the attenuating gene knockouts comprise ΔmucR, ΔvjbR, ΔmanB/A, ΔvirB2 ΔvirB2/ΔmanB/A mutant, ΔvjbR/ΔmucR mutant, ΔvirB2/ΔmucR mutant, ΔvirB2/ΔvjbR mutant, ΔvjbR/ΔmanB/A mutant, ΔmucR/ΔmanB/A mutant, or any combinations thereof and a marker for serological testing, wherein the marker is a differentiation of infected animals from vaccinated animals (DIVA) mutant;
(ii) an encapsulating agent comprising vitelline protein B capable of releasing the *Brucella* strain at a predetermined rate, and
(iii) an optional adjuvant or a pharmaceutically acceptable carrier.

BRIEF DESCRIPTION OF THE DRAWINGS

For a more complete understanding of the features and advantages of the present invention, reference is now made to the detailed description of the invention along with the accompanying figures and in which:

FIG. 5 shows INFγ production in BALB/c mice vaccinated with encapsulated *B. melitensis* vaccine strains as described in Example I. Blue bar=measurements performed after 10 weeks post-injection (p.i.); red bar=measurements performed after 30 weeks p.i.; yellow bar=measurements performed two days after challenge doses were delivered;

FIG. 6 shows INFγ production by spleen cells in BALB/c mice vaccinated with encapsulated *B. melitensis* vaccine strains as provided for in Example I. Double asterisks (**) represent data with $p<0.01$;

(FIG. 7B) The spleen weights were measured and used to compare the mutant strain to wild type organism. Statistical significance is based upon Student's T-Test comparing the deletion mutant to the wild type strain. The solid line at 0.69 logs represents the lower limit of detection, with is ≥5 CFU. Splenomegaly, a pathological consequence of infection with the wild type strain 16M is not observed with the vaccine strain 16MΔmucR;

Figure 9:
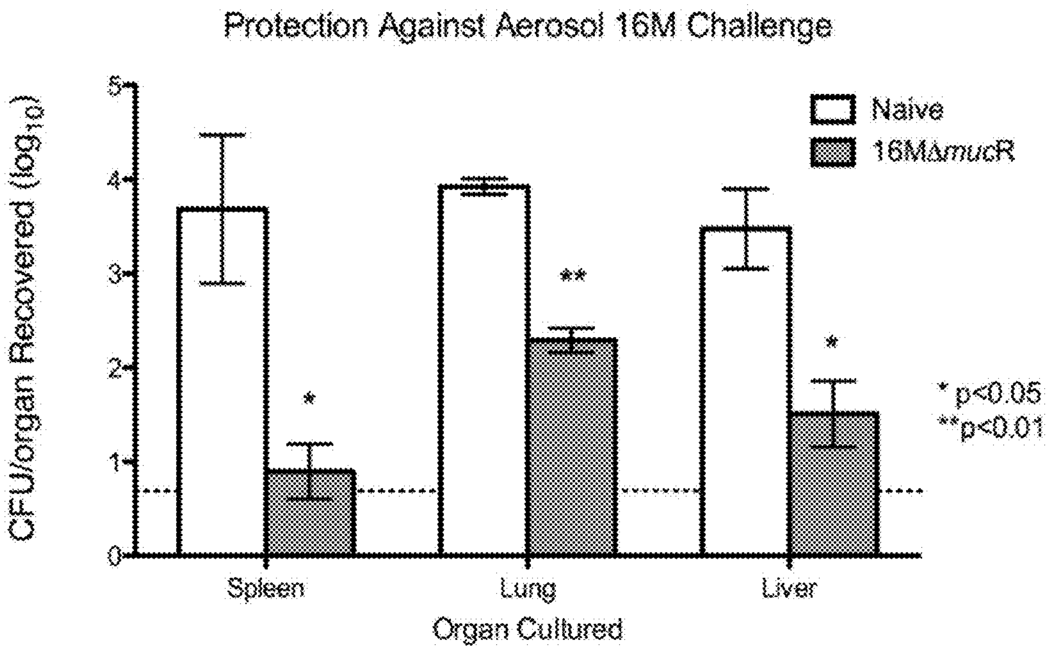
Figure 10A:
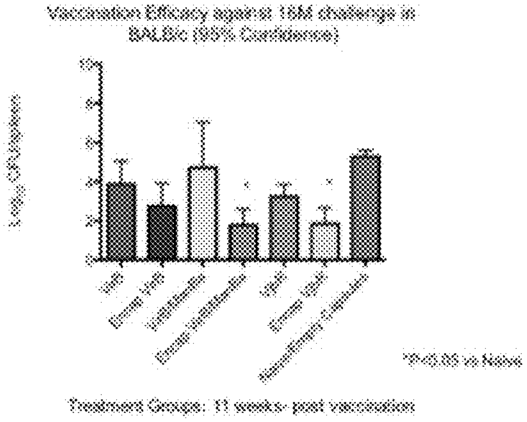
Figure 10B:
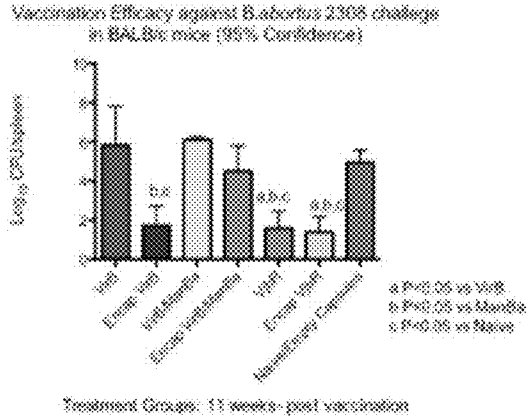
Figure 11:
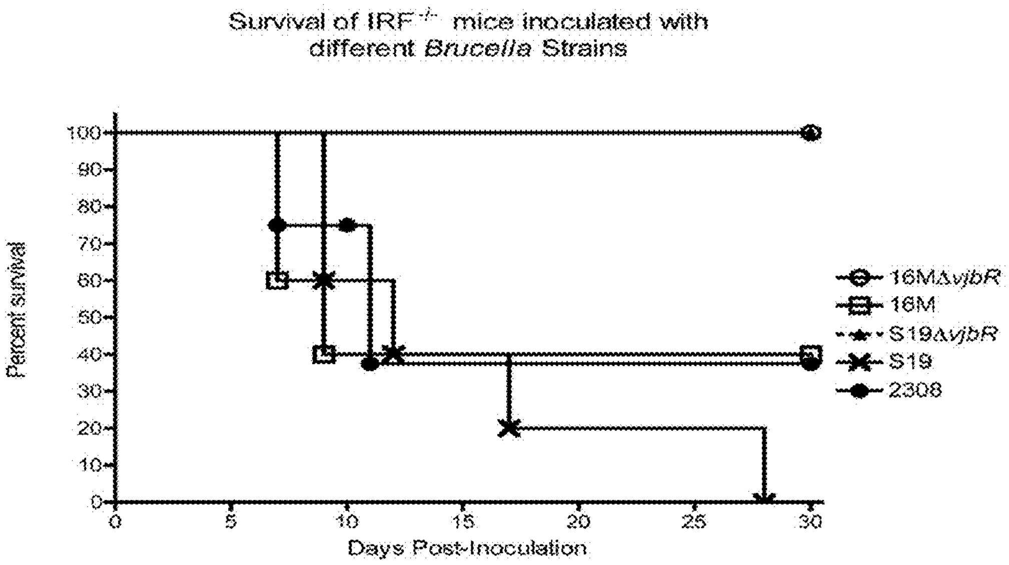
Figure 12A:
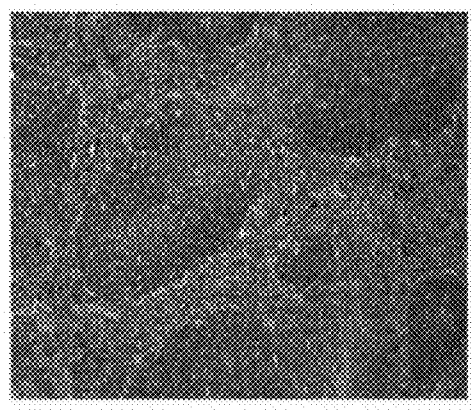
Figure 12B:
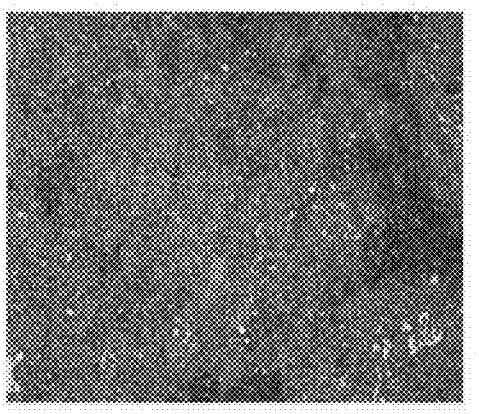
Figure 12C:
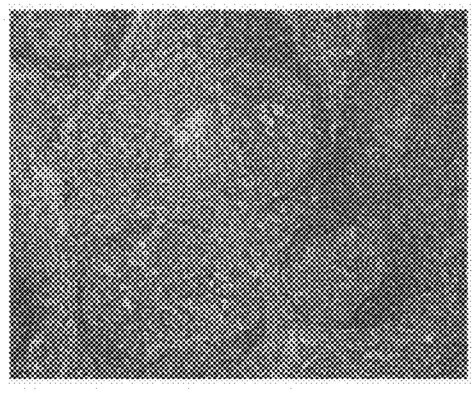
Figure 12D:
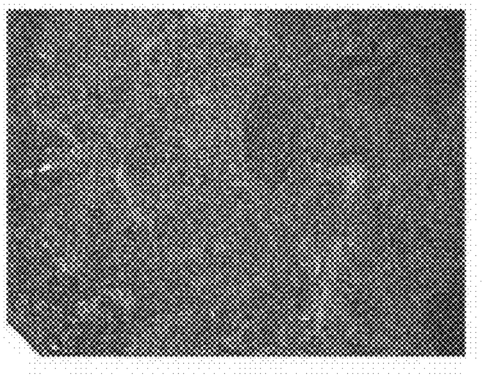
Figure 13A:
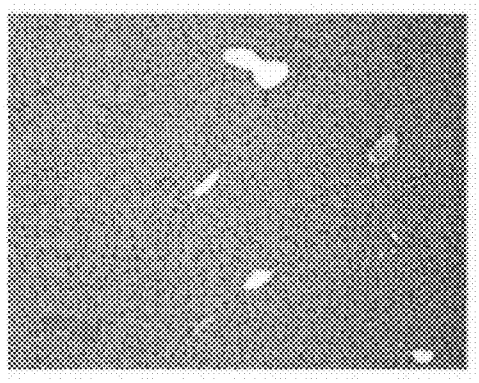
Figure 13B:
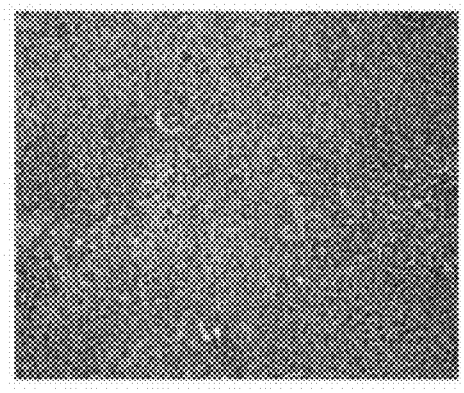
Figure 13C:
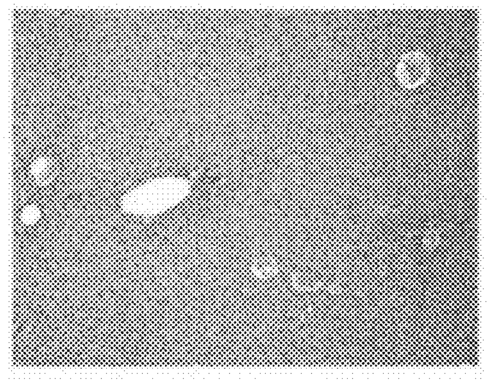
Figure 13D:
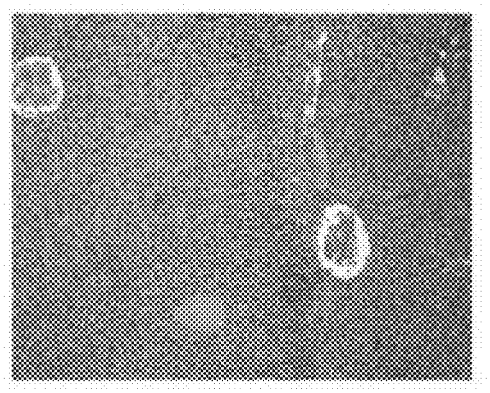
Figure 14A:
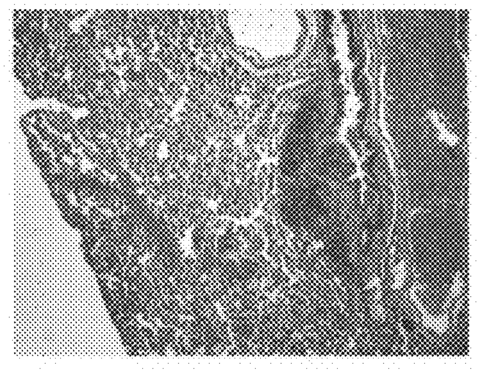
Figure 14B:
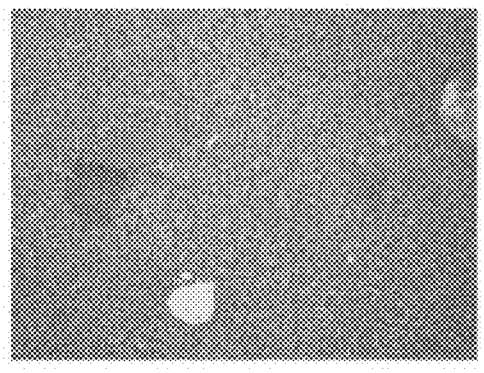
Figure 14C:
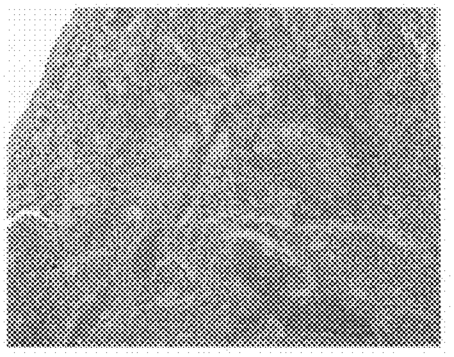
Figure 14D:
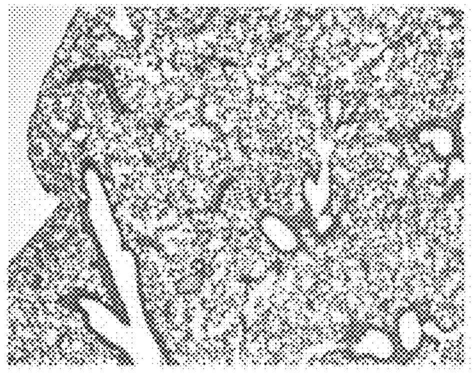
Figure 14E:
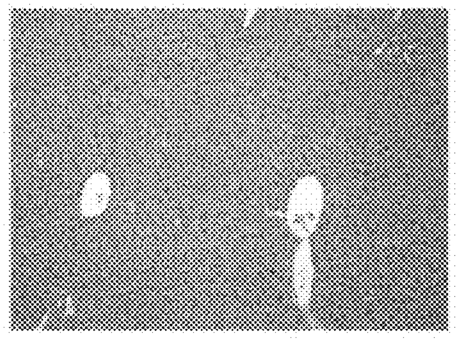
Figure 14F:
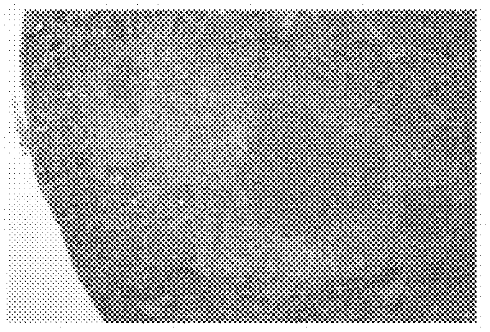

FIG. 9 shows the protection against homologous 16M aerosol challenge. Groups of 5 female BALB/c mice were vaccinated with 16MΔmucR at $1\times10^5$ CFU/mouse, or unvaccinated as a naïve control. 20 weeks post-vaccination all animals were challenged with an aerosol chamber dose of $5\times10^9$ CFU/ml of 16M. Four week post-challenge, mice were euthanized via $CO_2$ asphyxiation and spleens, livers, and lungs collected. Data are reported as the $\log_{10}$ recovery of *Brucella* from organs. The solid line at 0.69 logs represents the lower limit of detection, which is ≥5 CFU. Statistical analysis was performed by Student's T-Test comparing vaccinated to non-vaccinated mice for each organ separately;

FIGS. 10A and 10B show cross-protection against other species of *Brucella*. Six to eight week-old female BALB/c mice are inoculated intraperitoneally (IP) with a single dose ($1\times10^5$ CFU/mouse) of *B. melitensis* 16MΔVirB, 16MΔVirB/ManB/A, 16MΔvjbR. Controls include empty capsules or PBS as a control. Twenty weeks post-vaccination, mice (n=5 per group) were challenged i.p using $6\times10^5$ CFU/mouse of *B. melitensis* 16M (FIG. 10A) or *B. abortus* 2308 (FIG. 10B). One week post-challenge, animals were euthanized, spleens, lungs and livers harvested, homogenized in 1 ml of PBS and plated to determine total CFU/organ. Serial dilutions were performed and aliquots were plated onto TSA or Farrell's media plates. The levels of infection were expressed as means±SEMs of the individual $\log_{10}$ CFU/spleen, $\log_{10}$ CFU/liver and $\log_{10}$ CFU/lung;

FIG. 11 shows the survival of IRF-$1^{-/-}$ knockout mice infected with $1\times10^6$ CFU/mouse of either 2308, S19, S19ΔvjbR, 16M or 16MΔvjbR. Mice inoculated with ΔvjbR vaccine candidates survived longer compared to either 16M (P<0.005), 2308 (P<0.005) or S19 (P<0.005) In the present study, the safety of the vaccine candidates in the Interferon regulatory factor (IRF$^{-/-}$) knockout mice. IRF-$1^{-/-}$ mice infected with either wild-type *Brucella melitensis* 16M or the vaccine strain *Brucella abortus* S19, succumb to the disease within the first three weeks of infection, which is characterized by a marked granulomatous and neutrophilic inflammatory response that principally targets the spleen and liver. In contrast, IRF-1 mice inoculated with either the *B. melitensis* 16MΔvjbR or *B. abortus* S19ΔvjbR, do not show any clinical or major pathologic changes associated with vaccination. Additionally, when 16MΔvjbR or S19ΔvjbR vaccinated mice are challenged with wild-type *Brucella melitensis* 16M, the degree of colonization in multiple organs is significantly reduced, along with associated pathologic changes. These findings demonstrate the safety and protective efficacy of the vjbR mutant in an immunocompromised mouse model;

FIGS. 12A-12D shows microscopic changes observed in the spleens of IRF-$1^{-/-}$ mice vaccinated with S19ΔvjbR (FIG. 12C) or 16MΔvjbR (FIG. 12D) and challenged 8 weeks post-vaccination with $1\times10^6$ CFU/mouse of wild-type *B. melitensis* 16M. Nave but challenged mice (FIG. 12B) or naïve (FIG. 12A) are present for comparison. Note the marked reduction in the inflammatory response in the spleen in animals that received the ΔvjbR mutant;

FIGS. 13A-13D shows microscopic changes observed in the livers of IRF-$1^{-/-}$ mice vaccinated with S19ΔvjbR (FIG. 13C) or 16MΔvjbR (FIG. 13D) and challenged 8 weeks post-vaccination with $1\times10^6$ CFU/mouse of wild-type *B. melitensis* 16M. Naïve but challenged mice (FIG. 13B) or naïve (FIG. 13A) are present for comparison. Note the marked reduction in the inflammatory response in the liver in animals that received the ΔvjbR mutant; and FIGS. 14A-14I illustrate histological changes associated with 16MΔmucR vaccination followed by challenge with 16M strain. BALB/c mice were vaccinated with 16MΔmucR at $10^5$ CFU/mouse or left unvaccinated as naive controls. At 20 weeks post vaccination, all of the animals were challenged with an aerosol chamber dose of $5\times10^9$ CFU of 16M/ml. At 2 weeks post-challenge, tissues were collected for histology. The histology of the nonvaccinated but challenged animals (FIGS. 14A-14C) were compared to vaccinated but challenged animals (FIGS. 14D-14F). The lungs (FIGS. 14A and 14D), livers (FIGS. 14B and 14E), and spleens (FIGS. 14C and 14F) were compared to determine the reduction in pathology afforded by vaccination with the 16MΔmucR mutant. Naive mice are depicted (FIGS. 14G-141) for comparison. Hematoxylin and eosin staining was used (×10 magnification).

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an," and "the" are not intended to refer to only a singular entity, but include the general class of which a specific example may be used for illustration. The terminology herein is used to describe specific embodiments of the invention, but their usage does not delimit the invention, except as outlined in the claims.

As used herein, "*Brucella*" refers to a genus of Gram-negative bacteria. They are small, non-motile, encapsulated coccobacilli. While not limiting the scope of the present invention, *Brucella* is often transmitted by ingesting infected food, direct contact with an infected animal, or inhalation of aerosols.

As used herein, "splenomegaly" refers to a disease characterized by an enlargement of the spleen. While not limiting the scope of the present invention, symptoms of splenomegaly include but are in no way limited to abdominal pain, early satiety due to splenic encroachment or anemia related symptoms.

As used herein, the term "brucellosis" refers to a disease caused by ingestion of milk or meat and/or contact with the bodily fluids or secretions of animals infected with *Brucella* bacterial species. While not limiting the scope of the present invention, symptoms of brucellosis include but are not limited to acute undulating fever, headache, night sweats, fatigue, sterility and anorexia.

As used herein, the terms "prevent" and "preventing" include the prevention of the recurrence, spread or onset of a disease or disorder. It is not intended that the present invention be limited to complete prevention. In some embodiments, the onset is delayed, or the severity of the disease or disorder is reduced.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

The term "subject" as used herein refers to any mammal, preferably a human patient, livestock, or domestic pet. It is intended that the term "subject" encompass both human and non-human mammals, including, but not limited to bovines, caprines, ovines, equines, porcines, felines, canines, etc., as well as humans. In preferred embodiments, the "subject" is a ruminant (e.g. bovine, etc.) or a human although it is not intended that the present invention be limited to these groups of animals.

As used herein the term "immunogenically-effective amount" refers to that amount of an immunogen required to generate an immune response (e.g. invoke a cellular response and/or the production of protective levels of antibodies in a host upon vaccination).

In a specific embodiment, the term "pharmaceutically acceptable" means approved by a regulatory agency of the federal or a state government or listed in the U.S. Pharmacopeia or other generally recognized pharmacopeia for use in animals, and more particularly in humans.

The term "carrier" as used herein refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

The present invention relates to methods and compositions for the treatment of *Brucella* induced diseases and disorders. In preferred embodiments, the invention relates to vaccines. In additional embodiments, the invention relates to formulations capable of releasing said live vaccines at a controlled rate of release in vivo. In further embodiments, the invention relates to modified strains of the bacteria *Brucella melitensis* and *Brucella abortus*. In still further embodiments, the invention relates to compositions that do not induce splenomegaly in a subject receiving said compositions.

In preferred embodiments, the present invention relates to the treatment and prevention of Brucellosis induced diseases and disorders. To date, *Brucella* species have been isolated from humans and domesticated animals in nearly 90 countries, with an estimated 500,000 new cases each year. Moreover, *Brucella* species exhibit desirable characteristics for use as bioterrorism agents as described in Kaufmann et al. (1997) *Emerging Infectious Diseases* 3, 83-94 and Pappas et al. *Cell Mol Life Sci* (2006) 63, 2229-36, incorporated herein by reference. Thus, vaccines exhibiting prolonged interaction with the immune system combined with the safety of attenuated *Brucella* strains deliverable vaccines would be desirable.

A further embodiment of the present invention involves the use of double knockout, live *B. melitensis* mutants that are delivered orally using microencapsulation-mediated controlled release compositions. These compositions are storage-stable and compatible with a number of pharmaceutical agents. At this time and following decades of testing, the only effective vaccines for the prevention of brucellosis are living *Brucella* cells that stimulate the immune system through limited infection. Alternatives to the use of live, attenuated *Brucella* vaccines, including subunit vaccines and killed *Brucella*, have thus far proven non-efficacious. Live *Brucella* vaccines have been applied for decades to prevent brucellosis in cattle and sheep, but their capacity for direct use in humans has remained elusive. Previous reports have postulated that use of attenuated strains appropriate for use in humans is difficult, since spontaneously derived strains retain some level of virulence and are genetically undefined as disclosed in Spink et al. (1962) *Bulletin of the WHO* 26, 409-19, incorporated herein by reference. Recent evaluation of attenuated mutants has confirmed the superiority of long-term survival in stimulating a protective immune response, yet the added safety of short-term survival cannot be overlooked in the development of human vaccines. The present invention combines the optimal features of prolonged interaction with the immune system with enhanced safety of highly attenuated, single and/or double gene deletion *Brucella* mutants as a composition that is safe, free of side effects and efficacious in humans.

While not limiting the scope of the present invention in any way, ruminant transmission of *Brucella* may occur as a result of abortion of the fetus and/or shedding in milk. The best approach to minimize animal disease and subsequent transmission to humans is to block transmission via contact with aborted material or to prevent the consumption of contaminated dairy products. Inhibiting replication in reproductive tissues prevents the release of massive numbers of organisms into the environment. For example, *B. abortus* S19 vaccine does not replicate in the pregnant uterus due perhaps in part to erythritol present in elevated amounts in the pregnant uterus, although other defects may exist as disclosed in Williams et al. (1962) *British Journal of Experimental Pathology* 43, 530-537, incorporated herein by reference. *B. melitensis* Rev-1, a streptomycin-sensitive organism isolated following back-selection from a streptomycin-dependent organism, is used to protect against *B. melitensis* infections worldwide as provided for in Alton et al. *Journal of Comparative Pathology* (1967) 77, 293-300, incorporated herein by reference. Both S19 and Rev-1 provide protection in ruminants despite long-term persistence in a percentage of vaccinates, but retain significant virulence in humans as disclosed in Spink et al. *Bull World Health Organ* (1962) 26, 409-19. There are even reports of human isolation of the recently approved vaccine strain RB51, a rough derivative used with some success in ruminants as described in Palmer et al. Am J Vet Res (1997) 58, 472-7, but with less success in other species Arenas-Gamboa et al. (2009) 45, 165-73 incorporated herein by reference. While not limiting the present invention to any particular theory, there is evidence that the absence of the immunodominant O-antigen prevents development of cross-reacting immune responses that are indistinguishable from wild-type infection, but also increases the susceptibility of this strain to complement-mediated lysis, limiting survival and vaccine efficacy. Splenocytes in infected animals express more mRNA for IL-2, IFNγ, and IL-10, and less mRNA for IL-4 than uninfected animals, suggesting a T-helper type 1 (TH1) response as disclosed in Zhan and Cheers. Infection and immunity (1995) 63, 720-3, incorporated in its entirety by reference. However, increases in IL-10 may be counter-productive and may explain the virulence of this organism and the failure of some vaccines to stimulate a protective immune response as disclosed in Svetić et al. International immunology (1993) 5, 877-83, incorporated herein by reference. Subunit and killed vaccine candidates have proven to be less effective than live, attenuated organisms, despite the use of adjuvants, conjugation to carriers, immunization (+/−cytokines), or alternate routes of inoculation. Attempts to develop subunit vaccines have met with limited success as disclosed in Cassataro et al. Infect Immun (2005) 73, 8079-88 and Kaushik et al. Vet Res Comm (2010) 34, 119-32, both are incorporated here by reference. The intracellular nature of this organism requires the stimulation of a cell-mediated immunity (Th1) favored by the use of attenuated live vectors capable of stimulating this arm of the immune system. For this reason *Brucella*, like *M. bovis* BCG has been suggested as a vector for the delivery of immunogens of other intracellular agents as provided for in Surendran et al. Vet *Micorbiol* (2010) in press. One approach to human vaccine design is the identification of mutants of reduced persistence (survival) within macrophages based on the relationship to disease and potential for latent survival as disclosed in Hong et al. (2000) *Infection and Immunity* 68, 4102-4107, incorporated herein by reference. To date, functions targeted for inactivation are based on observations with other bacterial pathogens that typically cause acute infections. The chronic nature of brucellosis in humans suggests another approach is warranted. For this reason, the present inventors have identified gene functions necessary for persistence within macrophages using signature-tagged mutagenesis as disclosed in Lestrate et al. *Mol Microbiol* (2000) 38, 543-51, Foulongne et al. *Infect Immun* (2000) 68, 1297-303 and Hong et al. (2000) *Infect Immun* 68, 4102-4107, incorporated herein by reference. In this approach, genes required for survival have been classified into two groups. Group I gene functions are required for early survival in mice and are reduced at both two weeks and eight weeks post infection. A subgroup of these mutants recovers to normal levels by eight weeks suggesting that its function is only transiently required. Group II gene functions are required for long-term survival appearing normal at two weeks, but reduced after eight weeks. Although persistence in animal species may be acceptable, assuming the organism does not colonize tissues that threaten other animals in the herd or humans, use in humans requires much greater attenuations. Examination of the vaccine potential of these groups of organisms in the mouse model is performed here to provide proof of principle prior to testing in other species including non-human primates.

In some embodiments, the present invention is administered to human beings for the treatment and/or prevention of brucellosis. The hallmarks of human brucellosis are persistant undulating severe fevers coupled with a measurable splenomegaly with increased lymphohistiocytic cells in the spleen, a reduced percentage of splenic CD4+ and CD8+ T cells, and an increased percentage of splenic macrophages. Brucellosis occurs in at least 90 countries in humans or animals, which is often difficult to recognize, and may present as an acute fever, or as a chronic or localized infection. Infection is best diagnosed by growing the bacterium from blood or other infected tissues. Due to the slow growth of *Brucella*, cultures may require several weeks for positive identification. Infection is also diagnosed by detection of anti-*Brucella* specific antibodies in patients' blood. Humans are infected through the ingestion of contaminated animal products, and are normally dead-end hosts, although anecdotal evidence suggests occasional sexual transmission as disclosed in Meltzer et al. *Clin Infect Dis*. (2010) 51, e12-5, incorporated herein by reference. Persistence within the cells and tissues of the host is the basis for human disease and the cause of reduced efficacy of antibiotic treatment. Recommended treatment requires a combination of deoxycycline and gentamicin or rifampin as disclosed in Roushan et al. *J Antimicrobi Chemother* (2010) 65, 1028-35, hereby incorporated by reference. Disease may begin abruptly or gradually from three days to several months after exposure. Nonspecific symptoms typically observed in humans include pyrexia, diaphoresis, fatigue, loss of appetite, and muscle or joint pain. Depression, cephalalgia, and irritability also frequently occur. Infection of bones or joints occurs in about 1 in 3 patients, causing localized inflammation and edema. Some may also have cough, chest pain, and stomach upset. Although about 1 in 4 patients with brucellosis have respiratory symptoms, thoracic radiographs usually appear normal as disclosed in Madkour M M (1989) in *Brucellosis*, pp. 131-139. Lubani, et al (1989) *Quart J Med* 71, 319-324., both of which are incorporated by reference. Less common, but of added concern are infection of the brain, heart valves, or male reproductive system. Symptoms often last for 3-6 months, but occasionally persist for a year or longer and may reappear after periods of quiescence. Chronically infected patients frequently experience weight loss, and many patients temporarily improve but relapse as provided for in Ariza, et al (1986) *Antimicrob. Agents Chemother.* 30, 958-960., incorporated herein by reference. Brucellosis can be treated with antibiotics (usually doxycycline and rifampin) taken orally, but requires treatment for at least six weeks. Recurrence of human brucellosis may be related to a latent form of survival demonstrated to occur at low frequency as provided for in Ray et al (1988) *J. Am. Vet. Med. Assoc.* 192, 182-186, incorporated herein by reference.

*Brucella* organisms can be delivered via aerosol to infect humans. The use of *Brucella* as a weapon was calculated to pose a substantial financial risk as disclosed in Kaufmann et al. (1997) *Emerging Infectious Diseases* 3, 83-94 and Pappas et al. *Cell Mol Life Sci* (2006) 63, 2229-36, both incorporated herein by reference. Infection incapacitates human hosts with mostly flu-like symptoms, but will result in death if left untreated as provided for in Young E J (1995) *Clin Inf Dis* 21, 283-290, hereby incorporated by reference. Bioengineering poses the additional risk of introducing antibiotic resistance, rendering ineffective the most successful form of treatment. The transposon Tn10 encoding tetracycline resistance has been used to obtain stable transformants. The financial impact study did not attempt to determine the threshold at which financial risk may pose a risk to national security. Nor did the study outline scenarios in which the use of one organism might be favored over the use of others. The study did underscore the need to invest in research in all understudied organisms to prevent their use in this manner and suggested that decreased study of these organisms increase the potential consequences resulting from their use as weapons. *Brucella* spp. have been weaponized by several countries, including the former Soviet Union, Japan and the USA, and thus is a recognized biological warfare threat that can cause illness and death in humans. No vaccine for humans is available against this threat. Expected market and commercial need: The primary need for human brucellosis vaccines is for specialty protection of military personnel, public health workers and veterinarians with the cross-over opportunity for extensive markets in the high risk zones that occur throughout the world, particularly in the Middle East, Central Asia, Latin-America, Africa and the Far East. While there is a huge need for a human brucellosis vaccine world-wide, the question is whether or not major biologics manufacturers will recognize these needs as a profitable market, thus it is more plausible that federal government subsidized stockpiles, e.g., Bioshield I and Bioshield II, to protect the general public and military personnel represent a more likely market. The potential reluctance of the general population to use live vaccines is based on a limited trust of scientists and government, and such thinking must not be used to deter the development of products based on otherwise sound scientific principles. The use of such vaccines in humans is expected under extreme circumstances, such as stockpiling large reserves for protection against biological terrorism or biological warfare. Starting with the work of Louis Pasteur, live vaccines have offered the best possible solution for immune protection. Use in humans requires that safety be determined beyond a shadow of a doubt. This is one of the reasons that the present inventors use of double knock-out mutants. Questions concerning the preliminary production under Good Manufacturing Procedures and safety testing of such products warrant studies in non-human primate models.

As previously mentioned, no federally approved or commercially available human brucellosis vaccines are available anywhere worldwide; there simply are no currently known or published existing vaccine alternatives to protect humans from *Brucella*.

The present invention provides for controlled release compositions further comprising attenuated, live *Brucella* mutant vaccines. Drug delivery materials have historically been derived from many sources including commodity plastics and textile industries and have been incorporated into vehicles as diverse as pH responsive hydrogels and polymer microparticles or implants designed for surface or bulk erosion as disclosed in Langer RaP, N. A. (2003) *Bioengineering, Food and Natural Products* 49, 2990-3006., incorporated herein by reference. In the case of controlled release formulations, a drug is typically released by diffusion, erosion or solvent activation and transport. In most cases, the desired polymer characteristics include biocompatibility, lack of immunogenicity, capability of breakdown by the body and water solubility. Many of the processes used to entrap pharmaceuticals involve harsh organic solvents which are bacteriocidal and capable of denaturing proteins. When considering controlled release vehicles for the entrapment of active enzymes or living cells, new alternatives are needed. A number of milder processes based on established technologies and variations have recently been applied to the delivery of active protein agents such as insulin, erythropoietins and chemokines as provided for in Marschutz et al (2000) *Biomaterials* 21, 1499-07. Takenaga et al (2002) *J Control Release* 79, 81-91. and Qiu et al (2003) *Biomaterials* 24, 11-18., all of which are incorporated by reference, or as encapsulants for living cells to permit transplantation as disclosed in Young et al (2002) *Biomaterials* 23, 3495-3501, hereby incorporated by reference. The technologies cover a wide range of materials including gelatin-based hydrogels, protein-PEG microparticles, novel PEG copolymers, biodegradable PLGA particles, PLG/PVA microspheres and surface modified nanospheres. Alginate, a naturally occurring biopolymer, is especially well suited to the entrapment of living cells. Alginate is a linear unbranched polysaccharide composed of 1-4'-linked β-D-mannuronic acid and α-L-guluronic acids in varying quantities. Alginate polymers are highly water-soluble and easily crosslinked using divalent cations such as $Ca2+$ or polycations such as poly-L-lysine as provided for in Wee & Gombotz (1998) *Adv Drug Deliv Rev* 31, 267-285, hereby incorporated by reference. The relatively mild conditions required to produce either an alginate matrix or particle is compatible with cell viability. Entrapment in alginate has been shown to greatly enhance viability and storage as provided for in Cui et al (2000) *Int J Pharm* 210, 51-59 and Kwok et al (1989) *Proc. Int. Symp. Control. Release Bioact. Mater.* 16, 170-171, both of which are incorporated by reference. The physical properties such as porosity, rate of erosion, and release properties may be modulated through mixing alginates of different guluronic acid composition and through applying different coatings to the matrix as provided for in Wee & Gombotz (1998) *Adv Drug Deliv Rev* 31, 267-285. While in no way limiting the scope of the present invention, it is generally thought that release of a biomolecule from alginate matrices generally occurs through i) diffusion through pores of the polymer or ii) erosion of the polymer network. In general, the alginate matrix is stabilized under acidic conditions, but erodes slowly at pH of 6.8 or above.

The present invention exploits the performance and safety of live *Brucella* strains stabilized in an alginate bead for slow erosion of the capsule, resulting in a prolonged release of bacteria. A further advantage of the present invention is that highly attenuated, safe, double gene deletion, live *Brucella* mutants can be safely delivered orally by controlled release to optimally provide the long term immunostimulation required for protective immunity. As previously mentioned, currently available *Brucella* vaccines are unsuitable for human use, and antibiotic therapies are at best unreliable and ineffective, particularly if, e.g., bioterrorists introduce antibiotic resistance into weaponized strains of *B. melitensis*. Vaccination offers the best approach for long-range protection. In view of the lack of success of defining *Brucella* protective immunogens over the last four decades, the use of attenuated vaccine strains offers the best approach. Data reported below includes the identification of genetic defects that specifically attenuate intracellular survival. These strains have been characterized based on safety and attenuation in the mouse and goats and soon in non-human primates. The most protective strains are less attenuated, survive longer in the host and cause unwanted side effects (e.g., splenomegaly). The aim of the proposed studies is to utilize the most attenuated mutants and enhance vaccine potential through sustained release ultimately in non-human primates, to list a very specific and defined product. However, if successful the approach would provide proof of principle regarding the use of sustained delivery with live attenuated agents by providing direct evidence by i) potentiating the efficacy of weakly persistent strains, and ii) testing the persistence and safety of vaccine strains under conditions of controlled release for safety of controlled release vaccines and efficacy in mouse model as well as orally vaccinating with encapsulated mutant strains and challenged through the aerosol route. There is strong promise for oral vaccination with alginate and alginate/protein encapsulated strains as disclosed in Arenas-Gamboa et al. *Infect Immun* (2008) vol. 76, 2448-55, Kahl-McDonagh et al (2007) *Infect Immun* 75, 4923-32, Suckow et al (2002) *J Control Release* 85, 227-235, Kim et al (2002) *J Control Release* 85, 191-202., all of which are hereby incorporated by reference. In addition, lyophilization of bacteria in alginate beads extends their viability. Embodiments of the present invention include a storage-stable delivery system that may be administered orally and is generally applicable to a number of select agents.

In preferred embodiments, capsule formulations include vitelline protein B (vpB), a slowly erodable, non-antigenic protein, which extends the time frame over which capsule dissolution occurs. The present invention utilizes the ability of naturally occurring protein polymers (vpB) to act as controlled release vehicles. The proteins utilized for this purpose are encapsulants produced in nature that are unusually refractive to the actions of proteases, strong acids and bases. In some embodiments, alginate is formulated into the present invention. Alginate, a naturally occurring biopolymer, is especially well suited to the entrapment of living cells. Alginate is a linear unbranched polysaccharide composed of 1-4'-linked β-D-mannuronic acid and α-L-guluronic acids in varying quantities. Alginate polymers are highly water-soluble and easily crosslinked using divalent cations such as $Ca^{2+}$ or polycations such as poly-L-lysine as disclosed in Wee & Gombotz (1998) *Adv Drug Deliv Rev* 31, 267-285, incorporated herein by reference. The relatively mild conditions required to produce an alginate matrix or particle are compatible with cell viability; and in may cases, entrapment in alginate has been shown to greatly enhance viability and storage as disclosed in Cui et al (2000) *Int J Pharm* 210, 51-59. and Kwok et al (1989) *Proc. Int. Symp. Control. Release Bioact. Mater.* 16, 170-17.1, incorporated herein by reference. Release from alginate matrices generally occurs through i) diffusion through pores of the polymer or ii) erosion of the polymer network. In the case of standard bacterial entrapment methods used for BCG or for bifidobacteria as provided for in Cui et al (2000) *Int J Pharm* 210, 51-59., cells escape through erosion rather than diffusion due to size and surface charge. In general, the alginate matrix is stabilized under acidic conditions, but erodes slowly at pH of 6.8 or above. Capsule formulations additionally include vpB, a slowly erodable, non-antigenic protein, which extends the time frame over which capsule dissolution occurs. Ongoing research has identified *Brucella* genes required at different stages of infection. Extensive vaccine trials in laboratory species have revealed that inactivation of "early" genes, important early in infection, results in rapid clearance of the organism. The use of live, attenuated mutants in which "early" genes are inactivated or deleted, is favored, due primarily to the absence of side effects associated with long-term carriage of the organism. Work with "late" mutants, identified by their importance late in infection has confirmed that persistence of vaccine strains is associated with improved protective immunity. However, accompanying this increased efficacy is an increased risk of side effects. In order to avoid the rapid clearance of the early mutants or the side effects associated with late mutants, the present inventors use microencapsulation to provide a controlled release and enhanced immune response to mutants that survive for brief periods. Although other approaches are possible, the work proposed offers an opportunity to build upon historical use of attenuated live vaccine strains to protect against *Brucella* infections. Alternative sources of protection, including subunit or killed vaccine preparations have provided little promise for success. The development of the proposed product takes full advantage of ongoing research using signature-tagged mutagenesis and specific knock-out mutants that has identified genes required for survival coupled to novel microencapsulation and nanoencapsulation technology to balance attenuation, persistence and protective immunogenicity.

In one embodiment the present invention describes preparation of *B. melitensis* loaded alginate microspheres. Alginate beads were prepared by resuspending $6\times10^7$ CFU of the live *B. melitensis* mutant in 1 ml of 3-[N-morpholino] propanesulfonic acid] (MOPS) buffer comprising 10 mM MOPS, 0.85% NaCl, pH 7.4 and is mixed with 5 ml of alginate solution (1.5% sodium alginate, 10 mM MOPS, 0.85% NaCl, pH 7.3). Spheres were obtained by extruding the suspension through a 1.2 cm tip into a 100 mM calcium chloride solution and stirred for 15 min by using a Nisco Encapsulator. After extrusion of the bacterium-alginate mixture into the $CaCl_2$, the capsules were washed twice with MOPS for 5 min and further cross-linked with 0.05% poly-L-lysine (molecular weight. 22,000; Sigma) and 2.5 mg of VpB for 10 min. After two successive washes, the beads were stirred in a solution of 0.03% (wt/vol) alginate for 5 min to apply a final outer shell and washed twice with MOPS before storage at 4° C.

Pharmaceutical Formulations: The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). In one embodiment, the vaccine is encapsulated using materials described in U.S. Patent Application Publication No. 2005/0260258, hereby incorporated by reference.

In a preferred embodiment, the active compound and optionally another therapeutic or prophylactic agent are formulated in accordance with routine procedures as pharmaceutical compositions adapted for administration to human beings. Typically, the active compounds for administration are solutions in sterile isotonic aqueous buffer. Where necessary, the compositions can also include a solubilizing agent. Compositions for administration can optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the active compound is to be administered by infusion, it can be dispensed, for example, with an infusion bottle containing sterile pharmaceutical grade water or saline. Where the active compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for an oral administration of the active compound. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate can also be used. Oral compositions can include standard vehicles such as mannitol, lactose, starch, magnesium stearate, sodium saccharine, cellulose, magnesium carbonate, and the like. Such vehicles are preferably of pharmaceutical grade.

Further, the effect of the active compound can be delayed or prolonged by proper formulation. For example, a slowly soluble pellet of the active compound can be prepared and incorporated in a tablet or capsule. The technique can be improved by making pellets of several different dissolution rates and filling capsules with a mixture of the pellets. Tablets or capsules can be coated with a film that resists dissolution for a predictable period of time. Even the parenteral preparations can be made long acting, by dissolving or suspending the compound in oily or emulsified vehicles, which allow it to disperse only slowly in the serum.

Compositions for use in accordance with the present invention can be formulated in conventional manner using one or more physiologically acceptable carriers or excipients.

Thus, the compound and optionally another therapeutic or prophylactic agent and their physiologically acceptable salts and solvates can be formulated into pharmaceutical compositions for administration by inhalation or insufflation (either through the mouth or the nose) or oral, parenteral or mucosal (such as buccal, vaginal, rectal, sublingual) administration. In some embodiments, the administration is ophthalmic (e.g. eyes drops applied directly to the eye). In one embodiment, local or systemic parenteral administration is used.

For oral administration, the compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound. The microencapsulated vaccine gives a controlled release or continual boosting effect. Those formulations with vpB and alginate are described in U.S. Patent Application Publication No. 2005/0260258, hereby incorporated by reference.

For buccal administration the compositions can take the form of tablets or lozenges formulated in conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compositions can be formulated for parenteral administration by injection, e.g., by bolus injection or continuous infusion. Formulations for injection can be presented in unit dosage form, e.g., in ampoules or in multi-dose containers, with an added preservative. The pharmaceutical compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

In addition to the formulations described previously, the compositions can also be formulated as a depot preparation. Such long acting formulations can be administered by implantation (for example subcutaneously or intramuscularly) or by intramuscular injection. Thus, for example, the pharmaceutical compositions can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

In certain preferred embodiments, the pack or dispenser contains one or more unit dosage forms containing no more than the recommended dosage formulation as determined in the Physician's Desk Reference ($62^{nd}$ ed. 2008, herein incorporated by reference in its entirety).

Methods of administering the active compound and optionally another therapeutic or prophylactic agent include, but are not limited to, parenteral administration (e.g., intradermal, intramuscular, intraperitoneal, intravenous and subcutaneous), epidural, and mucosal (e.g., intranasal, rectal, vaginal, sublingual, buccal or oral routes). In a specific embodiment, the active compound and optionally other prophylactic or therapeutic agents are administered intramuscularly, intravenously, or subcutaneously. The active compound and optionally other prophylactic or therapeutic agents can also be administered by infusion or bolus injection and can be administered together with other biologically active agents. Administration can be local or systemic. The active compound and optionally the prophylactic or therapeutic agent and their physiologically acceptable salts and solvates can also be administered by inhalation or insufflation (either through the mouth or the nose). In a preferred embodiment, local or systemic parenteral administration is used.

Pulmonary administration can also be employed, e.g., by use of an inhaler or nebulizer, and formulation with an aerosolizing agent, or via perfusion in a fluorocarbon or synthetic pulmonary surfactant. In certain embodiments, the active compound can be formulated as a suppository, with traditional binders and vehicles such as triglycerides.

Selection of a particular effective dose can be determined (e.g., via clinical trials) by a skilled artisan based upon the consideration of several factors, which will be known to one skilled in the art. Such factors include the disease to be treated or prevented, the symptoms involved, the subject's body mass, the subject's immune status and other factors known by the skilled artisan.

The dose of the active compound to be administered to a subject, such as a human, is rather widely variable and can be subject to independent judgment. It is often practical to administer the daily dose at various hours of the day. However, in any given case, the amount administered will depend on such factors as the viability of the active component, the formulation used, subject condition (such as weight), and/or the route of administration.

Method of creating knockout mutants: The starting strain already has one of the mutations ΔvjbR, ΔmucR, ΔvirB2, ΔvirB2/ΔManB/A. The method has been previously described (25). The DIVA mutations include Δasp24, Δbcsp31, ΔvirB12.

Recombinant plasmid construction: In order to construct vectors to eliminate genes of interest, primers were designed to amplify sequences flanking the genes. These flanking regions are referred to as the 5' and the 3' fragments and were joined to one another using specially designed PCR primers (Table 1). Importantly, the reverse primer of the 5' fragment and the forward primer of the 3' fragment include approximately 5 to 10 nucleotides of sequence complementary to the opposite fragment and a terminal restriction site. The 5' and 3' fragments were amplified in separate reactions, gel purified, and used as templates for a second round of PCR (38). The forward primer of the 5' fragment and the reverse primer of the 3' fragment were utilized in a second round of PCR to engineer a product that represented the ligation of the 5' and 3' fragments. The ends of this joined product were removed by restriction digestion at sites engineered into the primers. The final fragment was gel purified and ligated to pBluescript II KS(+) (Stratagene). A kanamycin cassette was inserted between the 5' and 3' fragments following amplification via PCR from the plasmid pKD4 using primers containing the compatible restriction site located within the overlap between the fragments. pKD4 contains nptII from Tn5 flanked by FLP recombination target sites (11). These constructs are referred to as the marked plasmids (Table 2). The construction of the plasmid for creation of unmarked deletion mutants entails cloning of the original overlapping PCR product (lacking the kanamycin cassette) into plasmid pEX18Ap, which contains sacB, using the appropriate restriction enzymes (23). This construct is referred to here as the unmarked plasmid (Table 2) (25).

TABLE 1

Primers used in this study.

| Primer name | Sequence (restriction enzyme engineered) | Fragment |
|---|---|---|
| TAF101 | 5'-GGAATTCGGCAAAGCGAGTGGGTGATTAG-3'(EcoRI) (SEQ ID NO: 1) | asp24 upstream |
| TAF102 | 5'-CGGGATCCTGAGCAAGTGCGGGAATAGC-3'(BamHI) (SEQ ID NO: 2) | asp24 upstream |
| TAF103 | 5'-CGGGATCCTGGGAATGGAGCGGCTTTAG-3'(BamHI) (SEQ ID NO: 3) | asp24 downstream |
| TAF104 | 5'-GCTCTAGATTTGAACACTTGGCGATAGCG-3' (XbaI) (SEQ ID NO: 4) | asp24 downstream |
| TAF300 | 5'-CGGGATCCCGCACGTCTTGAGCGATTGTGTAGG-3'(BamHI) (SEQ ID NO: 5) | Kan cassette |
| TAF301 | 5'-CGGGATCCCGGGACAACAAGCCAGGGATGTAAC-3'(BamHI) (SEQ ID NO: 6) | Kan cassette |
| TAF356 | 5'-CGGGATCCCTGGAGGAAAACAATCTGGG-3' (BamHI) (SEQ ID NO: 7) | manB/A upstream |
| TAF357 | 5_-AAGACGGCGCGCCCGAACCTGTATCTGCCTG-3_(AscI) (SEQ ID NO: 8) | manB/A upstream |
| TAF358 | 5_-GTTCGGGCGCGCCGTCTTAACCCAAAACCGCTTCGTA-3_(AscI) (SEQ ID NO: 9) | manB/A downstream |
| TAF359 | 5_-GCTCTAGAGGGTTTTCTGATCGATCTGGTAGC-3_(XbaI) (SEQ ID NO: 10) | manB/A downstream |
| TAF204 | 5_-GGCGCGCCACGTCTTGAGCGATTGTGTAGG-3_(AscI) (SEQ ID NO: 11) | Kan cassette |
| TAF205 | 5_-GGCGCGCCGGACAACAAGCCAGGGATGTAAC-3_(AscI) (SEQ ID NO: 12) | Kan cassette |

TABLE 2

| Strain or plasmid | Relevant characteristic(s) |
|---|---|
| *B. abortus* strains | |
| 2308 | Wild type |
| Strain 19 | Vaccine strain |
| BAΔasp24::kan | Δasp24::Km |
| BAΔasp24 | Δasp24 |
| BAΔvirB2::kan | ΔvirB2::Km (polar) |
| BAΔvirB2 | ΔvirB2 (nonpolar) |
| BAΔmanBA | ΔmanBA |
| *B. melitensis* strains | |
| 16M | Wild type |
| Rev 1 | Vaccine strain |
| BMΔasp24::kan | Δasp24::Km |
| BMΔasp24 | Δasp24 |
| BMΔvirB2::kan | ΔvirB2::Km (polar) |
| BMΔvirB2 | ΔvirB2 (nonpolar) |
| BMΔmanBA::kan | ΔmanBA::Km |
| BMΔmanBA | ΔmanBA |
| *E. coli* strains | |
| DH5α | $F^-$ φ80dlacZΔM15 Δ(lacZYA-argF)U169 recA1 endA1 hsdR17($r_k^-m_k^+$) phoA supE44 λ thi-1 gyrA96 relA1 |
| Topl0 | $F^-$ mcrA Δ(mrr-hsdRMS-mcrBC) φ 80lacZΔM15 ΔlacX74 recA1 araΔ139 Δ(ara-leu)7697 galU galK rpsL ($Str^r$) endA1 nupG |
| DH10B | $F^-$ mcrA Δ(mrr-hsdRMS-mcrBC) φ 80lacZΔM15 ΔlacX74 recA1 endA1 araΔ139 Δ(ara-leu)7697 galU galK rpsL ($Str^r$) nupG |
| Plasmids | |
| pBluescript KS | ColE1, bla |
| pKD4 | FLP/FRT, $Km^r$ |
| pEX18Ap | sacB bla |
| pMMKB | TAF101/TAF104 cloned into pEX18Ap |
| pMMK8 | TAF101/TAF104 cloned into pBluescript |
| pMMK16 | pMMK8 separated by TAF300/TAF301 (kanamycin resistance) |
| pMMK29 | TAF356/TAF359 cloned into pBluescript |
| pMMK31 | TAF356/TAF359 cloned into pEX18Ap |
| pMMK33 | pMMK29 separated by TAF204/205 kanamycin resistance gene |
| pAV2.2 | Plasmid to make marked virB2 deletion |
| pAS1.1 | Plasmid to make unmarked virB2 deletion |

Bacterial strains and plasmids.

Selection of marked deletion mutants: Marked deletion mutants were created in *B. melitensis* and *B. abortus* via allelic exchange following electroporation of the marked plasmid into either 16M or S2308, respectively. Bacteria were grown as described above and pelleted via centrifugation at 1,700×g for 15 min at 4° C. All subsequent steps were performed on ice or at 4° C. The cell pellet was washed three times with ice-cold sterile water under the same conditions. After the final wash, the cells were resuspended in 1 ml sterile water. The bacterial cell suspension was used in each electroporation with approximately 1 g DNA in a prechilled 1-mm gap cuvette (Bio-Rad, California) and shocked in a BTX electroporation apparatus set at 2.2 to 2.5 kV and 246. SOC-B (6% [wt/vol] tryptic soy broth, 10 mM NaCl, 2.5 mM KCl, 10 mM $MgCl_2$, 10 mM $MgSO_4$, and 20 mM glucose) medium was immediately added to the cuvette, transferred to microcentrifuge tubes, and incubated overnight at 37° C. with agitation (31). Following incubation, the entire culture was plated onto TSA containing kanamycin. Colonies were replica plated onto TSA containing kanamycin and onto plates containing carbenicillin. Marked deletion mutants from allelic exchange should be kanamycin resistant (Kmr) and carbenicillin sensitive (Carbs). Verification of mutant genotypes was obtained via PCR and Southern blot analysis to ensure that the gene of interest was deleted and the kanamycin cassette was retained.

Selection of unmarked deletion mutants. The unmarked plasmid, containing the sacB gene, ligated 5' and 3' fragments, and bla gene, was used for electroporation into marked deletion strains. Electroporation conditions were identical to those described for the construction of marked mutants. Following electroporation, cells were plated onto TSA containing carbenicillin to select for the first homologous recombination, i.e., a cointegration. Colonies were replica plated onto sucrose plates (TSA without salt, containing 6% [wt/vol] sucrose, without antibiotic) and to TSA containing carbenicillin. Colonies that grew on carbenicillin (Carbr) but not sucrose (Sucs) were cointegrates with a functional sacB gene. Resolution of cointegration occurs spontaneously and was selected for by inoculating 5 ml of sucrose broth (TSB, without salt or antibiotics, and supplemented with 6% [wt/vol] sucrose) and incubating for 24 h with agitation at 37° C., with subsequent plating onto sucrose-containing medium. All knockout candidates were verified via PCR and Southern blot analysis to demonstrate gene deletion as well as loss of the kanamycin cassette.

The following examples are provided in order to demonstrate and further illustrate certain preferred embodiments and aspects of the present invention and are not to be construed as limiting the scope thereof.

In the experimental disclosure that follows, the following abbreviations apply: MOPS (3-[N-morpholino] propanesulfonic acid); PCR (polymerase chain reaction); vpB (vitelline protein B).

EXAMPLE I

The studies described herein focus on highly attenuated mutants in order to provide the highest degree of safety. Despite multiple hits in the same genes, sequencing in progress has identified more than 100 distinct loci that contribute to intracellular survival. Double mutants have been constructed in a number of the most attenuated mutants. Double mutants may include two genes in the same metabolic pathway at separate genetic loci to virtually eliminate the potential for reversion of the vaccine strain to virulence or distinctly different functions which when combined may be expected to severely cripple the organism or provide a diagnostic target in order to distinguish vaccine from virulent field strain. Transposon mutagenesis has identified several hundred *Brucella* genes whose activity contributes to intracellular survival as provided for in Ficht et al. (2000) *Infection and Immunity* 68, 102-107, incorporated herein by reference. Nonpolar knockout mutations have been constructed in a number of genetic loci identified as important for survival and protection induced by these strains against challenge was examined at several times post clearance. DNA flanking the internal deletion fragment was amplified by PCR using primers designed with specific restriction sites to create a nonpolar deletion and both fragments were cloned into pBluescript or any other ColE1-based vector that cannot replicate in *Brucella*. A kanamycin resistance cassette is inserted at the junction of the two fragments and the resulting plasmid is electroporated into the parental *Brucella* strain. Marked-knockouts were created by allelic exchange and selected based on their kanamycin resistance and ampicillin-sensitivity and were considered polar. These organisms are then subjected to a second electroporation using a plasmid that contains the same construct lacking the kanamycin cassette, but also has the sacB and ampicillin-resistance genes. Cointegrants were selected for carbenicillin resistance and sucrose sensitivity. This step assures the integration of a functional sacB gene necessary for the final step. These colonies are incubated in media containing sucrose and plated onto sucrose plates. Individual colonies are selected and replica plated onto sucrose plates and verified for kanamycin sensitivity and sucrose resistance. Verification of nonpolar knockout was performed by PCR, Southern blotting, and DNA sequencing.

In surveying the large numbers of transposon mutants developed, sequence data has provided a great deal of information concerning the environment in which *Brucella* persists. In a recent screen of mariner mutants, $^{40}/_{42}$ of the genes identified to date possess homology to entries in GenBank. Of these mutants, $^{31}/_{42}$ were either known virulence factors or had homology to virulence factors described in other organisms, $^{6}/_{42}$ were purine auxotrophs, $^{10}/_{42}$ were virB genes, and $^{2}/_{42}$ possessed no similarity to entries in the database. Based on the preliminary results at least 3% of the *Brucella* genome appears to be required for intracellular survival. Although, screening in the mouse model suggested at least a ten-fold higher number, it became too difficult to sort through mutants exhibiting lesser degrees of attenuation. It may be expected that attenuated mutants unable to persist within macrophages will fall into several different categories. Mutants exhibiting the greatest level of attenuation and are therefore safest will be the primary focus of this proposal. Genes involved in purine and glutamate (or nitrogen) metabolism have been identified within this group. Both provide a number of potential targets for elimination along complex pathways. Another group may be impaired in response to stress conditions, including those unable to withstand the bactericidal mechanisms of phagocytes such as the oxidative burst, acidity of the phagolysosome, or activity of defensins. A third group may have defects in effector molecule secretion for example by the *Brucella* homolog to the type IV secretion system. While not limited the present invention to any particular theory, it is possible that these molecules function to "modify the phagosome" and enhance survival or the equivalent of icm/dot. However, the inventors have also identified a number of novel classes of genes that will have to be fully characterized in order to establish their role in infection. Many in this final group may be defective in specific host adaptations, e.g. adhesion to host cells, invasion, intracellular replication, systemic spread, or modulation of the host immune response.

Figure 1:
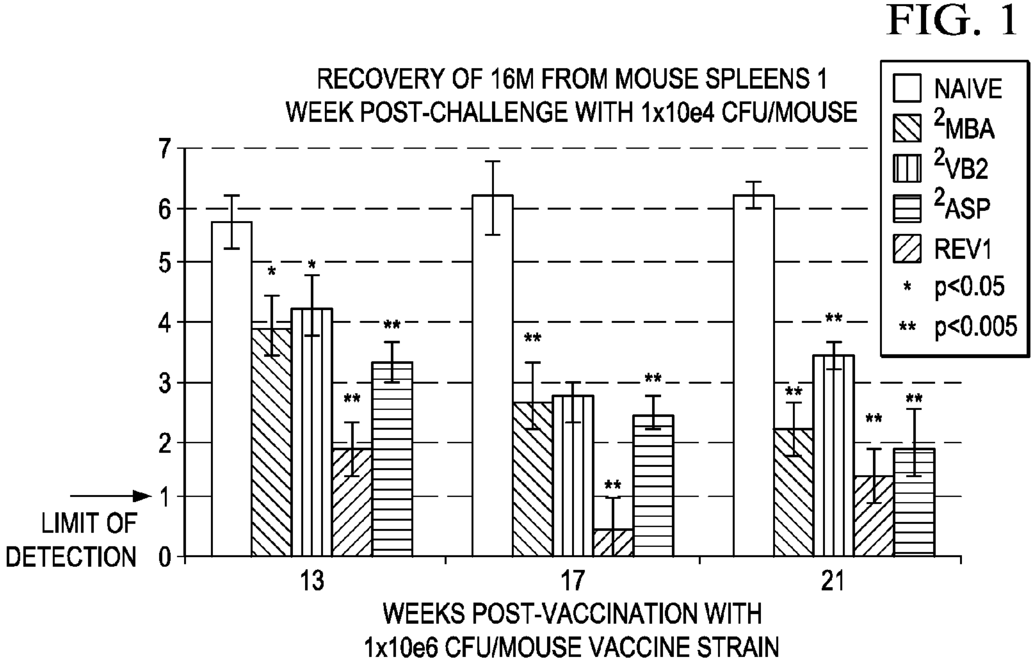
FIG. 1 shows protection of Balb/c mice vaccinated with the present invention against virulent challenge infection. Groups of five mice were vaccinated with $1\times10^6$ colony forming units (CFU) of vaccine strain and challenged at 12, 16 or 20 weeks post-vaccination. The spleens were removed one week later and virulent *B. melitensis* 16M colonies enumerated. Significant difference determined using ANOVA is indicated by either an asterisk ($p<0.05$) or double asterisk ($p<0.01$)

One embodiment of the present invention involves the use of mutations in recognized *Brucella* virulence factors to develop vaccines. Both single and double mutations have been investigated to provide a balance between safety and persistence. While double knockouts likely provide the highest degree of safety, some of these mutants will be too highly attenuated to stimulate protective immunity even in encapsulated form or may be missing important protective antigens. For purposes of this proposal, the present inventors utilized knockouts whose identity and putative function are known. These include ΔvirB2 (type IV secretion system) and ΔmanB/A (LPS synthesis). Efficacy of these single mutant strains alone is illustrated here (FIG. 1); vaccine potential of individual mutants was evaluated following clearance of vaccine candidates (i.e., nonrecoverable) in order to minimize the contribution of non-specific immune functions to clearance.

*B. melitensis* Rev-1 (vaccine strain) was also used as a control in the protection experiment. When considering clearance of these organisms following vaccination, manB/A (ΔMBA), virB (ΔVB2) exhibit early, rapid declines in recovery (Group 1 classification, highly attenuated), while the ΔASP (Group 2) mutant exhibits a more gradual decline in number; the double mutant virB/manB/A exhibits the most rapid clearing time. The results observed (FIG. 1) appear to confirm the contention that increased protection is associated with persistence of vaccine strains. However, it is difficult to generalize since genes missing from the mutants may also be important protective immunogens. The ΔVB2 shown here and the ΔVB2/ΔMBA double mutant may be used effectively in one embodiment of the present invention. The efficacy and persistence of the organisms introduced in unencapsulated or encapsulated (controlled release) format may further be evaluated. The inventors hypothesize that maximal safety may be through use of the rapidly clearing strains, while enhancing efficacy through the disclosed controlled release format.

Figure 2:
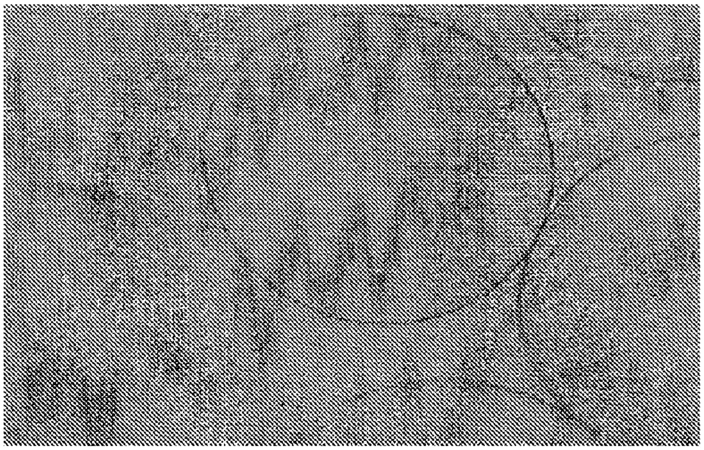
FIG. 2 shows a micrograph of alginate reservoir capsules measuring 200 microns in diameter.

The use of a novel biopolymer, vpB, in microcapsule formulations greatly extends the time frame of erosion and release of capsule contents. This property is based on the unusual enzymatic and chemical resistance of the protein to breakdown. To demonstrate the unusual properties of this protein additive with regard to vaccination, the present inventors have included it in both a solid microparticle and a reservoir microparticle formulation (alginate, FIG. 2), and monitored the enhancement of the immune response in each case. Our methods include the addition of vpB (recombinant) derived from aquatic invertebrates, a protein of 31 kDa produced in *E. coli* free of additional amino acids and purified through conventional chromatography. The protein is non-antigenic and has been extensively characterized regarding biochemical properties. We have demonstrated the ability to form a variety of capsules with this material altering the surface properties and controlled release profiles of the particles (data not shown). The performance of vpB containing reservoir capsules in vaccine enhancement is shown in FIG. 6. Armed with the information that the vpB protein imparted sustained release profiles to erodible capsules, the inventors used this protein as an additive to extend release profiles of a number of capsule types. Alginate capsules in particular were a target of interest as a hydrogel to stabilize entrapped vaccine strains and maintain viability. Through a modification of the methods of Abraham et al. (1996) *Pharm. Dev. Technol.* 1, 63-68, hereby incorporated by reference, the present inventors produced three formulations of alginate-based microcapsules to entrap and deliver live *Brucella* vaccines. Alginate solutions (1.5% in MOPS buffer) containing $1\times10^6$ bacteria/ml were nebulized into a solution of 100 mM $CaCl_2$ using an Encapsulator with a 200 micron nozzle (Innova, Inc.) and stirred for 15 minutes at 20° C. $CaCl_2$ solution was removed and crosslinking of alginate achieved with a solution of 0.5% poly-L-lysine. An external coating of alginate was applied through a five-minute incubation of particles in a 0.03% (w/v) alginate solution in MOPS buffer. Particles were washed with MOPS buffer before storage at 4° C. (formulation A). A second formulation employed the substitution of vpB for poly-L-lysine in the crosslinking reaction, producing a vpB layer in the capsule wall (formulation C). A third formulation incorporated vpB (0.5 mg/ml) into the alginate core with the bacterial payload to extend bacterial release from the capsule and delay breakdown of the capsule (formulation B). Formulations A, B, and C were compared with unencapsulated bacteria, empty capsule type C and buffer for protection against challenge 32 weeks after a single vaccination dose as shown in FIG. 6. Each of three capsule formulations described above were tested in mice (FIG. 6) through intraperitoneal injection to perform as a depot. The vaccine strain used 19C6 (ΔvjbR; BMEI1116) is one of the Group 1 attenuated strains discovered through transposon mutagenesis of *B. melitensis*. This has been revealed by screening attenuated strains in macrophage culture and mice. In this study $1\times10^6$ bacteria 19C6 were introduced into mice (n=10) intraperitoneally (IP). The six groups of animals received buffer alone (MOPS), empty capsules (alginate), unencapsulated 19C6 or one of three encapsulated forms of 19C6. The three forms include formulation A (alginate only), formulation B (alginate, vpB core) and formulation C (alginate, vpB shell). Thirty-two weeks following vaccination, all groups were challenged with $1\times10^4$ *B. melitensis* strain 16M through IP injection. Vaccination of mice with the 19C6 strain alone provided three logs of protection against challenge. Vaccination with the same organism in an encapsulated form provided one to two logs of additional protection. Formulation C, which provided the best protection, is formulated with a vpB shell; 50% of the animals in this group demonstrated sterile immunity after challenge, thirty-two weeks following vaccination.

Figure 3:
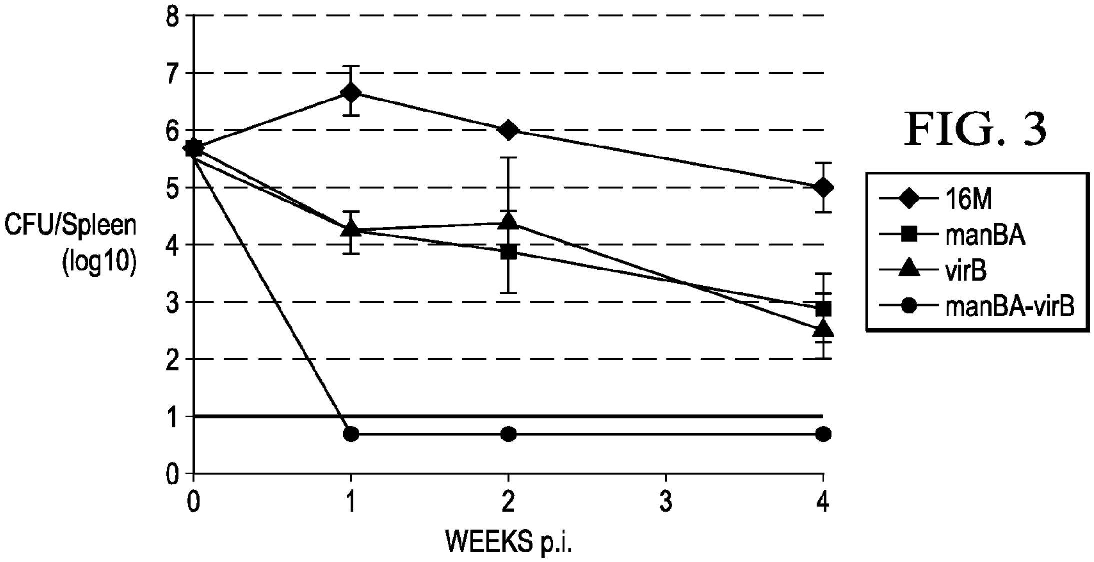
FIG. 3 shows clearance of *B. melitensis* vaccine strains from a mammalian spleen following inoculation of Balb/c mice with $1\times10^6$ cfu as provided for in Example I.

This study was carried out once with 60 mice and clearly demonstrates the utility of encapsulation in immune potentiation. The inventors used two highly attenuated strains for the studies described here. The present inventors determined the clearing time for encapsulated *Brucella* from the mouse spleen following vaccination as a measure of safety (FIG. 3). The present inventors have further tested a single mutant ΔVB and a double mutant, ΔVB/ΔMBA for persistence and efficacy in an encapsulated format.

Figure 4:
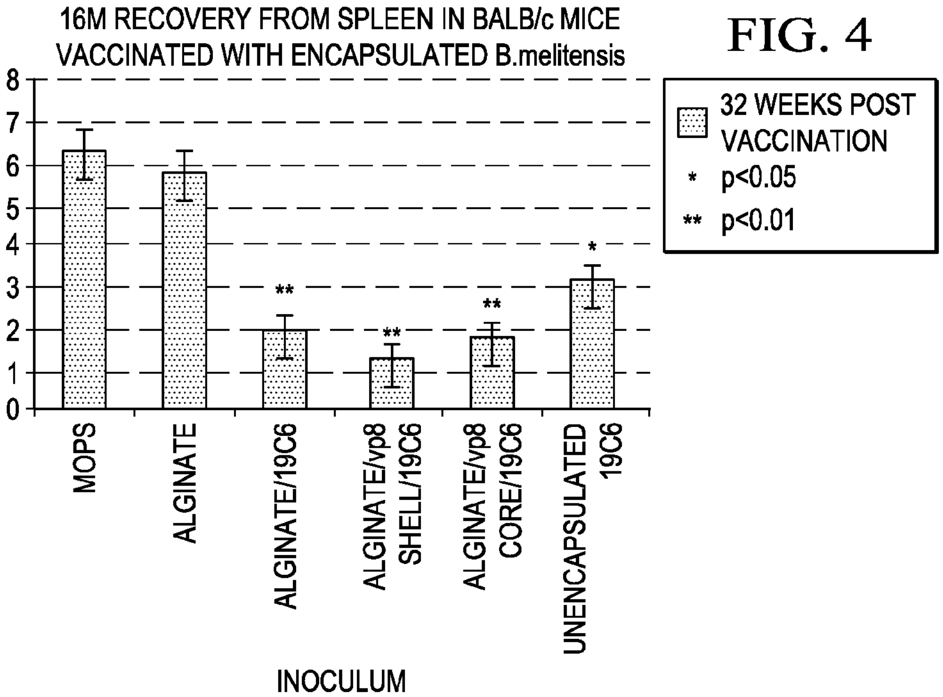
FIG. 4 shows recovery of *B. melitensis* 16M by bacteriologic culture from spleen in BALB/c mice vaccinated with encapsulated *B. melitensis* vaccine compositions of the present invention following 32 weeks post-vaccination as provided for in Example I. A single asterisk (*) represents data with $p<0.05$; double asterisks (**) represent data with $p<0.01$.

FIG. 4 shows recovery of *B. melitensis* 16M by bacteriologic culture from spleen in BALB/c mice vaccinated with encapsulated *B. melitensis* vaccine compositions of the present invention following 32 weeks post-vaccination. A single asterisk (*) represents data with p<0.05; double asterisks (**) represent data with p<0.01.

In related studies the inventors used cell fractionation and ELIspot analysis to define the T cell subpopulations producing the observed cytokines and have provided an ELISA-based Bioplex analysis here to illustrate an example of data collected to date on the experimental vaccination detailed in FIG. 6. Both humoral and cell mediated immunity were followed during the course of the study. Prior to challenge, five mice were evaluated for cell mediated immune status through splenocyte blastogenesis and release of cytokines into the supernatant (FIG. 6.). Following challenge the remaining mice were bled at 48 hours and serum evaluated for cytokine production. This same group was sacrificed at two weeks post challenge and an enumeration of bacteria in the spleen was used as an indicator of protection (FIG. 4). To summarize the analysis of immune parameters, the inventors found that serum antibody titers correlated with protection while blastogenesis results were unrevealing. Cytokine analysis of antigen-stimulated splenocytes reveals the hallmarks of a Th1 response in animals analyzed prior to challenge (FIG. 6). Bioplex analysis of cytokines present in sera revealed similar profiles. We will analyze T cell subpopulations via ELIspot in future experiments to gain a better understanding of immune correlates.

Cytokine quantitation: Spleens were excised from vaccinated mice and ground lightly with the frosted ends of two glass slides. Erythrocytes were lysed using ACK lysis buffer (150 mM $NH_4Cl$, 10 mM $KHCO_3$, 100 mM $Na_2EDTA$, pH 7.2-7.4) and the cell suspension was washed following centrifugation three times in RPMI-1640 medium. Then the concentration of cells was adjusted to $2\times10^6$ cells/ml with complete RPMI-1640 containing 25 mM HEPES, 2 mM L-glutamine, 10% (v/v) heat-inactivated (for 30 min at 56° C.) fetal bovine serum (Difco), and $5.5\times10^5$ M 2-mercaptoethanol in the presence of 100 U penicillin and 10 mg streptomycin (Difco). For cytokine production by splenocytes, $4\times10^6$ cells are cultured as described in a 24-well tissue culture treated plate (Costar, Massachusetts) for three days at 37° C., 5% $CO_2$. $1\times10^8$ heat-killed *B. melitensis* 16M, or 1 mg of lysate is applied to each well. Cells in control wells receive complete RPMI-1640 only as background control. Cell suspensions are harvested and assayed for cytokine levels. Filtrates were analyzed by ELISA using Bio-Plex analysis, a multiplex suspension array technique that relies on antigen capture and bioluminecence (Luminex Corp.) for IL-2, IL-4 and IL-10. Spleen supernatants were treated according to manufacturer's instructions. Sera were serially diluted and similarly analyzed. FIG. 6 shows the results of ELISA analysis via Bioplex of IFN gamma in spleen supernatants from animals at 32 weeks post-vaccination. FIG. 5 illustrates IFN gamma production detected in sera of animals at 10 and 30 weeks post-vaccination and two days after challenge doses were delivered. The relative levels of cytokines concur between these analyses although the levels of cytokine are much higher in spleen supernatants than in sera, as expected. Data has also been collected on IL-2, IL-4 and IL-10 revealing a Th1 cytokine profile elevated in IL2 and IFN gamma and low in IL4 production. One may further use ELIspot analysis to assign these values to specific T cell subsets.

EXAMPLE II

The present inventors have previously used signature-tagged mutagenesis to identify in vitro and in vivo virulence genes (1, 16, 40). Among these, a mucR (BMEI 1364) mutant, was attenuated for survival in the mouse and macrophage model (40). The role of MucR in *Brucella* is unknown, but recently, the function of the MucR gene has been identified in soil and plant bacteria such as *Agrobacterium tumefaciencis* and *Sinorhizobium meliloti* (19, 28). MucR is a transcriptional regulator that coordinates a diverse set of bacterial behaviors including the control of exopolysaccharide production which is important not only in bacterial-plant symbiosis but also in biofilm formation(4, 5).

In the present invention the inventors conducted a series of studies designed to characterize the *Brucella melitensis* 16MΔmucR as a potential vaccine candidate against intraperitoneal and aerosol *Brucella melitensis* 16M challenge. Vaccination with the mutant did not induce systemic or local adverse reactions and significantly protected BALB/c mice against intraperitoneal and aerosol challenge.

Materials and Methods: (i) Mice: 6 to 8-week old female BALB/c mice were obtained from the Jackson Laboratories (Bar Harbor, Me.) and acclimated for one week prior to infection or vaccination. All experimental procedures and animal care were performed in compliance with the institutional animal care guidelines.

Bacterial strains: Strains used in these studies include *B. melitensis* 16MΔmucR (engineered for this study and used as the vaccine candidate) and the virulent strain *Brucella melitensis* 16M biovar 1 (originally obtained from ATCC and re-isolated by this lab from an aborted goat fetus) (24). Bacteria were grown on tryptic soy agar (TSA) (Difco, Becton Dickinson) or Farrell's media (TSA supplemented with Oxoid *Brucella* supplement) at 37° C. with 5% $CO_2$. For construction of the *B. melitensis* 16MΔmucR knockout, the medium was supplemented with kanamycin (100 μg/ml), or carbenicillin (100 μg/ml). Sucrose media was utilized for sacB counterselection and unmarked gene deletion selection as previously described(25). *Escherichia coli* cultures utilized for the construction of the 16MΔmucR mutant were grown on Luria-Bertani (LB) (Difco, Becton Dickinson) plates or in LB broth overnight at 37° C. with or without ampicillin (100 mg/liter) or kanamycin (100 mg/liter).

To prepare organism for animal infections, *Brucella* were harvested from the surface of the plates after 3 days of incubation using phosphate-buffered saline (PBS) pH 7.2. The bacteria were pelleted and resuspended to a final concentration based on optical density readings using a Klett meter and a standardized curve. Actual viable counts were confirmed by serial dilution, plating, and enumeration.

Construction of the *Brucella melitensis* 16MΔmucR deletion mutant: The mutant was constructed as previously described with some modifications (25). The sequence upstream of the mucR gene (BMEI1364) was amplified from *B. melitensis* 16M with the primer pair 5'GCTCTAGAGC-CCATCAACAACAGGACAAACGG3' (SEQ ID NO: 13) (contains XbaI site) and 5'GGCGGCGCGCCTGGT-TGCTCCGAACTATGCTG (SEQ ID NO: 14) (contains AscI site). The sequence downstream of mucR was amplified with the primer pair 5'CCAGGCGCGCCGCCGCTGCG-TATTTCATAATC (SEQ ID NO: 15) (contains AscI site) and 5'GCTCTAGAGCCTTTGCAGGTTTTCCGTATCTTT (SEQ ID NO: 16) (contains XbaI site). These two products were ligated to one another via overlapping PCR via the AscI site (New England Biolabs) engineered between the two sequences. This overlap product was then ligated to pEX18Ap via the XbaI site (named pMMK40). A kanamycin resistance gene was subsequently ligated within the vector by the unique AscI site (plasmid pMMK44). This construct was used for electroporation into *Brucella melitensis* 16M. Potential marked deletion mutants were kanamycin resistant and carbenicillin sensitive, and were verified by PCR and Southern Blot; the confirmed mutant was named 16MΔmucR::Kan. The unmarked deletion mutant was engineered by electroporation of pMMK40 into 16MΔmucR::Kan and selected on TSA/carb@100. Co-integrants with the following phenotypes were selected: $Kan^R$, $Carb^R$, and $sucrose^S$, indicating a co-integrant with a functional sacB gene. Bacteria were selected in the presence of sucrose for resolution of co-integration as previously described(25). All knockout candidates were verified by PCR and Southern Blot to demonstrate gene deletion and loss of the kanamycin cassette.

Figure 7A:
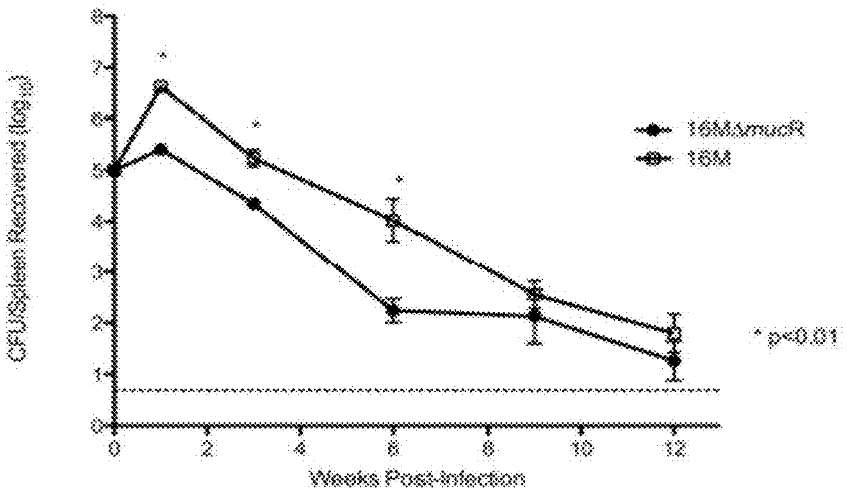
FIGS. 7A and 7B shows the kinetics of clearance of 16MΔmucR from mice. Forty, 6-8 week old female BALB/c mice were used to evaluate the persistence and replication of 16MΔmucR. Mice were inoculated intraperitoneally with either (FIG. 7A) $1\times10^6$ CFU in 100 μl 16MΔmucR or (b) $1\times10^6$ CFU in 100 μl of the parental strain 16M. Groups of four mice were euthanized via carbon dioxide asphyxiation at 1, 3, 5, 7 or 9 weeks post infection. At each time point, the spleens were harvested, weighed, and homogenized in 1 ml of peptone saline. Serial dilutions were prepared, and 100 μl aliquots of each dilution (including the undiluted organ) were plated in duplicate onto TSA plates. The levels of infection were expressed as the mean±of standard error of the mean (SEM) of individual log CFU/spleen.
Figure 7B:
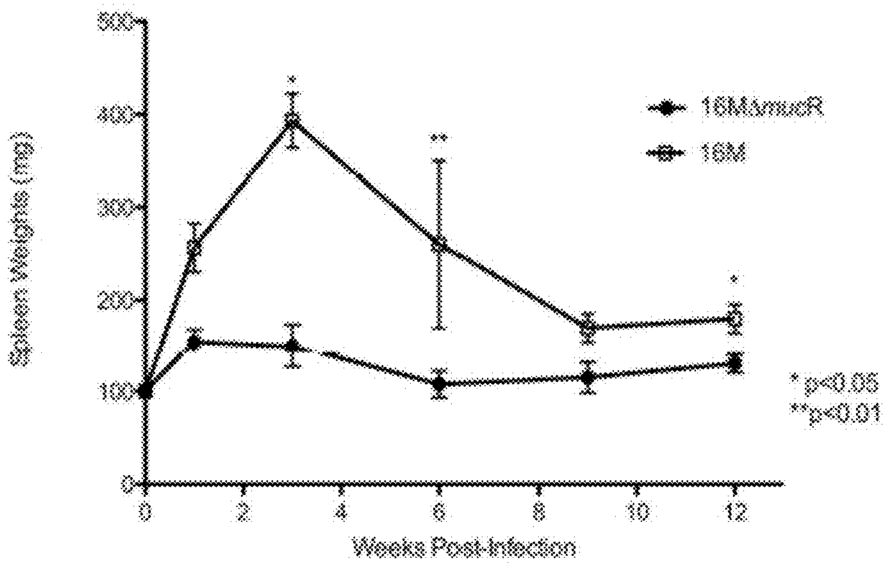

Evaluation of *B. melitensis* 16MΔmucR attenuation in mice: Forty, 6-8 week old female BALB/c mice were used to evaluate the persistence and replication of the *B. melitensis* 16MΔmucR mutant. Mice were inoculated intraperitoneally with either (a) $1 \times 10^6$ CFU in 100 μl 16MΔmucR or (b) $1 \times 10^6$ CFU in 100 μl of the parental strain 16M. Groups of four mice were euthanized via carbon dioxide asphyxiation at 1, 3, 5, 7 or 9 weeks post infection. At each time point, the spleens were harvested, weighed, and homogenized in 1 ml of peptone saline. Serial dilutions were prepared, and 100 μl aliquots of each dilution (including the undiluted organ) were plated in duplicate onto TSA plates. The levels of infection were expressed as the mean±of standard error of the mean (SEM) of individual log CFU/spleen (FIG. 7A). Elevated spleen weights indicative of splenomegaly in the 16M parental strain were not not observed in the vaccine strain (FIG. 7B).

Immunization of mice for efficacy studies: Six to eight week-old female BALB/c mice were distributed into 3 treatment groups and inoculated intraperitoneally (IP) with a single dose of *B. melitensis* 16MΔmucR. Treatment groups included: (a) $1 \times 10^5$ CFU/mouse, (b) $1 \times 10^6$ CFU/mouse, or (c) PBS as a control. Mice were housed for 20 weeks post-vaccination under ABSL-3 conditions.

Figure 8:
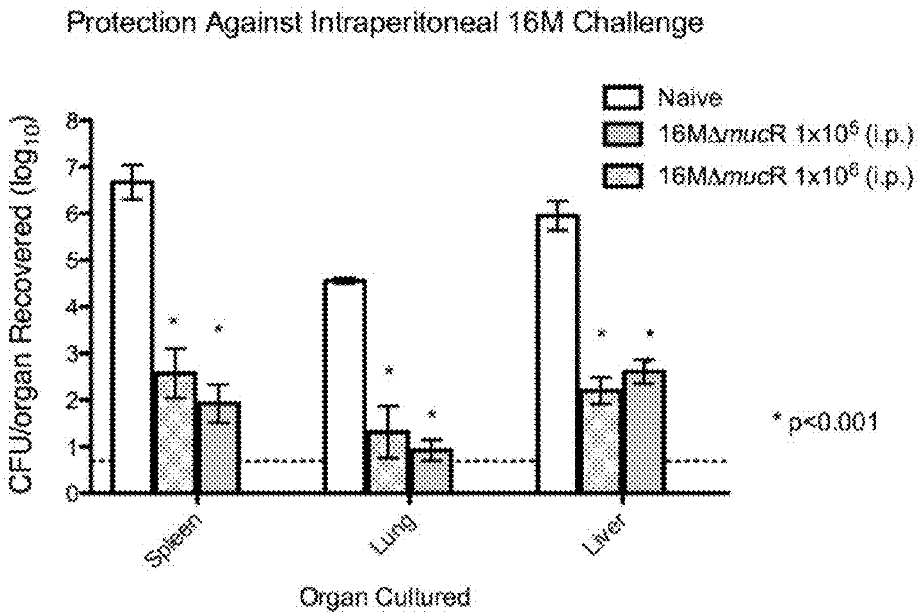
FIG. 8 shows the protection against homologous 16M intraperitoneal challenge. Groups of 5 female BALB/c mice were vaccinated with 16MΔmucR at either $1\times10^5$ CFU/ mouse, $1\times10^6$ CFU/mouse, or unvaccinated as a naïve control. 20 weeks post-vaccination all animals were challenged with $6\times10^5$ CFU/mouse IP. One week post-challenge, mice were euthanized via $CO_2$ asphyxiation and spleens, livers, and lungs collected. Data are reported as the $\log_{10}$ recovery of *Brucella* from organs. The solid line at 0.69 logs represents the lower limit of detection, which is ≥5 CFU. Statistical analysis was performed by ANOVA for each organ separately followed by Tukey's honestly significant (HSD) post-test comparing all groups to one another.

Vaccination efficacy against intraperitoneal challenge: Twenty weeks post-vaccination, mice (n=5 per group) were challenged i.p using $6 \times 10^5$ CFU/mouse of *B. melitensis* 16M. One week post-challenge, mice were euthanized via $CO_2$ asphyxiation. Spleens, lungs, and livers were collected, weighed and homogenized in 1 ml of PBS. Serial dilutions were performed and aliquots were plated onto TSA or Farrell's media plates. One week post-challenge, animals were euthanized, spleens, lungs and livers harvested, homogenized and plated to determine total CFU/organ. The levels of infection were expressed as means±SEMs of the individual $log_{10}$ CFU/spleen, $log_{10}$ CFU/liver and $log_{10}$ CFU/lung (FIG. 8).

Vaccination efficacy against aerosol challenge: Twenty weeks post vaccination, groups of 5 mice were challenged with an aerosol chamber dose of $5 \times 10^9$ CFU/ml of *B. melitensis* 16M. Four weeks post challenge, the mice were euthanized and the lungs, liver and spleen were removed, weighed, homogenized in 1 ml PBS, serially diluted and plated onto Farrell's medium to determine total CFU/organ. The levels of infection were expressed as means±of SEMs of the individual $log_{10}$ CFU/spleen, $log_{10}$ CFU/liver and $log_{10}$ CFU/lung. A group of 3 mice were euthanized directly after aerosol exposure to quantify the CFU/lung inhaled (FIG. 9).

Cross protection against other species of *Brucella*: Six to eight week-old female BALB/c mice are inoculated intraperitoneally (IP) with a single dose ($1 \times 10^6$ CFU/mouse) of *B. melitensis* 16MΔVirB, 16MΔVirB/ManB/A, 16MΔvjbR. Controls include empty capsules or PBS as a control. Twenty weeks post-vaccination, mice (n=5 per group) were challenged i.p using $1 \times 10^4$ CFU/mouse of *B. melitensis* 16M or *B. abortus* 2308. One week post-challenge, mice were euthanized via $CO_2$ asphyxiation. Spleens, lungs, and livers were collected, weighed and homogenized in 1 ml of PBS. Serial dilutions were performed and aliquots were plated onto TSA or Farrell's media plates. One week post-challenge, animals were euthanized, spleens, lungs and livers harvested, homogenized and plated to determine total CFU/organ. The levels of infection were expressed as means±SEMs of the individual $\log_{10}$ CFU/spleen, $\log_{10}$ CFU/liver and $\log_{10}$ CFU/lung. Cross protection was observed for encapsulated *B. melitensis* ΔvirB2 and for encapsulated *B. melitensis* ΔvjbR (FIGS. 10A and 10B).

Safety Studies with vjbR mutants in *B. melitensis, B. abortus* S19: IRF-/IRF- (interferon regulatory gene) knockout mice are considered a good model for immunocompromised subjects. IRF-$1^{-/-}$ mice were infected intraperitoneally with $1\times10^6$ CFU/mouse of either *B. melitensis* 16MΔvjbR, *B. abortus* S19ΔvjbR, *B. melitensis* 16M, *B. abortus* 2308 or S19 (FIG. 11). Mice inoculated with ΔvjbR vaccine candidates survived longer compared to either 16M (P<0.005), 2308 (P<0.005) or S19 (P<0.005) In the present study, the safety of the vaccine candidates in the Interferon regulatory factor ($IRF^{-/-}$) knockout mice. IRF-$1^{-/-}$ mice infected with either wild-type *Brucella melitensis* 16M or the vaccine strain *Brucella abortus* S19, succumb to the disease within the first three weeks of infection, which is characterized by a marked granulomatous and neutrophilic inflammatory response that principally targets the spleen and liver. In contrast, IRF-$1^{-/-}$ mice inoculated with either the *B. melitensis* 16MΔvjbR or *B. abortus* S19ΔvjbR, do not show any clinical or major pathologic changes associated with vaccination. Additionally, when 16MΔvjbR or S19ΔvjbR vaccinated mice are challenged with wild-type *Brucella melitensis* 16M, the degree of colonization in multiple organs is significantly reduced, along with associated pathologic changes. These findings demonstrate the safety and protective efficacy of the vjbR mutant in an immunocompromised mouse model.

Histopathology: Twelve female BALB/c mice were distributed into 4 groups. The groups consisted of A) 16MΔmucR vaccinated and subsequently aerosol challenged (2 weeks post-challenge) B and C) Non vaccinated (nave) and aerosol challenged (2 and 4 weeks post-challenge) and D) non vaccinated and IP challenged (4 weeks post-challenge). Animals were euthanized by $CO_2$ asphyxiation, and spleen, lungs, liver, kidneys and heart were harvested, fixed in 10% buffered formalin, paraffin embedded and stained with hematoxylin and eosin. Histological changes were assessed between treatment groups (FIGS. 12A-12D, and FIGS. 13A-13D).

Statistical analysis: Bacterial burden from mutant clearance as well as efficacy studies were expressed as mean CFU+/−standard error (SE) and presented graphically as the $\log_{10}$ CFU *Brucella* recovered per organ. Culture-negative organs were assigned a value of four CFU, which is below the limit of detection of five CFU/organ. Spleen weight data from kinetics was plotted as the mean spleen weight in mg+/−standard error (SE).

For the survival of 16MΔmucR in mice, a Student's T-test was performed to compare splenic colonization and weight of the knockout strain to the wildtype control group at each timepoint (FIGS. 7A and 7B). Efficacy studies compared vaccinated and subsequently challenged mice to mice receiving PBS as a vaccine control that were challenged with wild type organism. In the intraperitoneal challenge study, statistical significance of differences between vaccinates were analyzed by ANOVA for each organ separately followed by Tukey's honestly significant (HSD) post-test comparing all groups to one another (FIG. 8). In the aerosol protection studies a Student's T-test was performed for each organ separately to compare the vaccines to naïve mice. For all statistical analyses P-values less than 0.05 were considered statistically significant (FIG. 9).

Attenuation of 16MΔmucR in mice: To determine the effect of the mucR gene deletion in vivo, mice were infected IP with $1\times10^6$ CFU/mouse of *B. melitensis* 16MΔmucR. Compared to the wild type strain 16M, the colonization of the spleen with 16MΔmucR was significantly reduced at 1, 3 and 6 weeks (P<0.01), but not at 9 or 12 weeks (FIG. 7A). Reduced splenic colonization by the 16MΔmucR mutant correlated with reduced spleen weights (FIG. 7B), indicating a reduced inflammatory response by the mutant. Spleen weights of mice infected with wild-type 16M were consistently higher.

Evaluation of immune protection provided by 16MΔmucR against intraperitoneal 16M challenge: In order to determine the vaccination efficacy elicited by the 16MΔmucR mutant, the level of protection provided by the vaccine candidate was evaluated against intraperitoneal *B. melitensis* 16M wild-type challenge at 20 weeks postvaccination. Animals were euthanized one week post-challenge because this timepoint corresponds to the highest bacterial load in the spleen based on previous studies (25). At one week post challenge (21 weeks postvaccination), there was a statistically significant decrease in the splenic, hepatic and pulmonary bacterial loads from the mice vaccinated with the 16MΔmucR mutant relative to those of the naïve mice regardless of the vaccination dose, with a 4.14-4.75 log reduction in bacterial burden in the spleen (P<0.001), 3.24-3.34 log reduction in the liver (P<0.001) and 2.54-3.64 log reduction in the lungs (P<0.001) (FIG. 8).

Evaluation of immune protection provided by 16ΔmucR against aerosol 16M challenge: In order to determine the vaccination efficacy elicited by the 16MΔmucR mutant against a natural route of exposure, the level of protection provided by the vaccine candidate was evaluated against aerosol *B. melitensis* 16M wild-type challenge at 20 weeks postvaccination. For aerosol exposure studies, the four week post-challenge timepoint was chosen as the timepoint of peak splenic colonization(23). Mice that were euthanized within 1 hour of aerosol exposure inhaled an average of $2.1\times10^4$ CFU/lungs as determined by plating their lungs and enumerating the bacteria recovered.

When mice were challenged by the aerosol route, the 16MΔmucR vaccine candidate protected mice significantly in all organs plated. The mutant afforded a 2.79 log reduction in the bacterial burden in the spleen (P<0.05), 1.97 log reduction in the liver (P<0.05) and a 1.63 log reduction in the lungs (P<0.01) (FIG. 9).

Vaccination of mice with *B. melitensis* ΔvjbR strain protects against *B. abortus* challenge as well as *B. melitensis* challenge. There should be good cross protection whether a *B. abortus* or a *B. melitensis* strain is used as vaccine based on previously described data. Exception is ΔvirB/ΔManB (FIGS. 10A and 10B).

Survival of the *Brucella* ΔvjbR mutants in IRF-$1^{-/-}$ knockout mice: Ten days post inoculation, 60% of mice had succumbed to the infection with *B. melitensis* 16M (FIG. 11). Similarly, mice inoculated with *B. abortus* 2308 exhibited signs of illness by day 7 and 50% of mice were euthanized by day 11 post-inoculation due to imminent deterioration (FIG. 11). Interestingly, mice vaccinated with the vaccine strain S19, also elicited clinical signs of illness, but at a later timepoint than observed with the virulent strains, i.e., at day 10 post-inoculation with a 100% mortality rate by day 28 (FIG. 11). In contrast, 100% of mice vaccinated with either the 16MΔvjbR or S19ΔvjbR mutant exhibited no signs of disease (P<0.0001) and 100% survived beyond day 30 post-inoculation (FIG. 11). Two animals from the *B. melitensis* 16M and *B. abortus* 2308 exhibited no signs of disease beyond day 30 post-inoculation. This data clearly demonstrate that vjbR mutants are less virulent in immunocompromised mice than the parental strains from which they were derived.

Microscopic changes observed in the spleens (FIGS. 12A-12D) and in the livers (FIGS. 13A-13D) of IRF-$1^{-/-}$ mice vaccinated with S19ΔvjbR (FIGS. 12C and 13C) or 16MΔvjbR (FIGS. 12D and 13D) and challenged 8 weeks post-vaccination with $1\times10^6$ CFU/mouse of wild-type *B. melitensis* 16M. Naïve but challenged mice (FIGS. 12B and 13B) or naïve (FIGS. 12A and 13A) are presented for comparison. It can be seen from the figures that there is a marked reduction in the inflammatory response in both the spleen and liver in animals that received the ΔvjbR mutants.

Figure 14G:
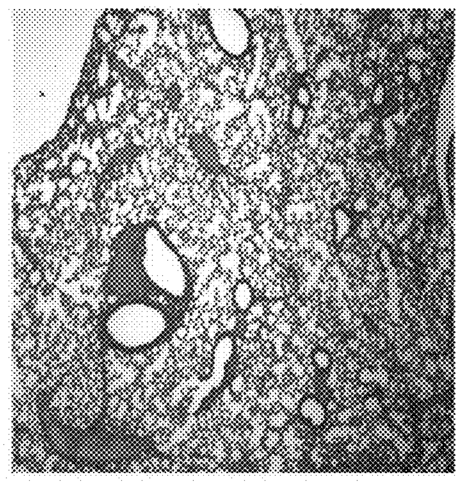
Figure 14H:
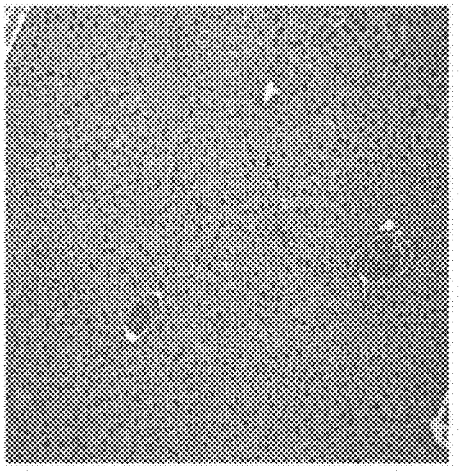
Figure 14I:
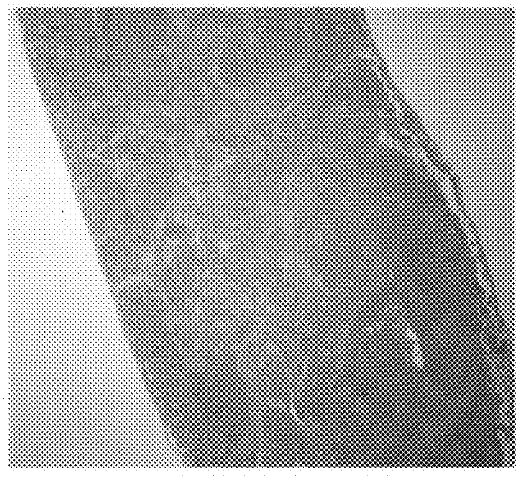

Evaluation of histological changes in mice vaccinated with 16MΔmucR: Histological analysis of the lungs, livers, and spleens of BALB/c mice inoculated with either 16M_mucR (FIGS. 14D-14F) or naive PBS controls (FIGS. 14A-14C) that were subsequently aerosol challenged with wild-type 16M and euthanized 2 weeks postchallenge was assessed to determine the degree of inflammation elicited by the challenge organism in animals that were vaccinated with the mutant. Histologically, the bronchiole-associated lymphoid tissue was prominent at 2 weeks postchallenge (FIG. 14A), and no significant changes were seen in mice vaccinated with the mucR mutant (FIG. 14D). Inflammatory foci in the liver of naive aerosol challenged mice were rare at 2 weeks postchallenge (FIG. 14B) and absent in mice vaccinated with the mucR mutant (FIG. 14E). Changes in the spleen of naive mice consisted of marked extramedullary hematopoiesis at 2 weeks postchallenge (FIG. 14C). There were no significant changes in the spleen of mice vaccinated with the mucR mutant (FIG. 14F). No significant changes were observed in the kidneys or hearts in vaccinated or aerosol exposed animals (data not shown). Naive mice are depicted in FIGS. 14G-14I for comparison.

Historically, the most efficacious vaccines against brucellosis have been live attenuated vaccines, and is the case of multiple currently licensed vaccine strains for animal use including S19, Rev 1 and RB51(15, 37). Unfortunately, both S19 and Rev 1 vaccines, which have been highly efficacious in controlling the disease in cattle and goats respectively, have proven to be unsafe or have the capacity to cause adverse reactions in humans due to local and systemic reactions that in some cases resulted in the development of the disease (3, 38). Other vaccinology alternatives including the use of subunit, recombinant proteins and DNA vaccines which might be safer for human use, although capable of eliciting both humoral and cellular immune responses to a certain degree, generally induce lower or no protection compared to the live attenuated vaccines in animal models (8-10, 14, 30, 32, 33, 36). As such, a live attenuated organism has been utilized as the vaccine type of choice for the prevention of Brucellosis. An ideal *Brucella* vaccine would be one that persists long enough to generate a robust immune response without eliciting the undesired side effects such as splenomegaly or clinical signs of disease.

Previous studies using signature tagged mutagenesis by the present inventors have identified multiple candidate genes that are attenuated for virulence and survival in the mouse and macrophage models, among these disruption of the mucR locus in *B. melitensis* 16M(40). The inventors have previously demonstrated an in vitro and in vivo role for the mucR transposon mutant. The organism was found to be significantly attenuated in both models when the gene was interrupted. To further characterize the role of mucR in regards to survival, protective efficacy and safety in vivo, an unmarked gene deletion was created.

In *Sinorhizobium meliloti*, a gram-negative soil bacterium that establishes a symbiotic relationship with alfalfa, a clear role of the mucR gene has been recently established(28). MucR has been identified as a transcriptional regulator with multiple functions that help in the establishment of symbiosis, including a key role in the control of exopolysaccharide biosynthesis, necessary for biofilm formation(4, 5, 35). Biofilms are microbial aggregates surrounded by a self-produced matrix that attach to a surface (11, 12). The biofilm provides bacteria with a physical barrier against antibiotics, innate defense mechanisms from the host and environmental stress conditions including UV radiation, pH changes and osmotic shock among others (11). Important components of biofilms include water, bacterial cells and exopolysaccharides(11). Exopolysaccharides have been recognized as key elements that provide the structural support for the biofilm. In order to ensure a successful symbiotic association, exopolysaccharide production and biofilm formation are tightly regulated and partially controlled by the mucR gene. Deletion of mucR in *S. meliloti* therefore results in deficiencies in invasion or the establishment of symbiosis.

One clear example of the importance of the mucR gene in *S. meliloti* symbiosis is in the induction of nodule formation (28). MucR causes an increase in the biosynthesis of nod factor, necessary for the induction of nodule development. Other established roles of mucR in this organism include an induction of increased expression of multiple operons required for nitrogen fixation and respiration, as well as numerous type IV secretion systems and putative transport-related genes all necessary for a successful symbiosis(28).

In the case of *Brucella*, the role of mucR is less understood. Preliminary studies from this laboratory using microarray technology suggests that the mucR gene regulates exopolysaccharide biosynthesis, as well as genes involved in iron sequestration and storage, nitrogen metabolism and stress response mechanisms. (J. Weeks, unpublished data). Although preliminary and still under investigation, all these putative roles of mucR in *Brucella* explain to a certain degree the attenuation of the mutant strain observed in J774A macrophages and in mice. Recently it has been reported that *B. melitensis* 16M produces an exopolysaccharide; studies suggested that *Brucella* may indeed be capable of biofilm formation (17). It is possible that mucR may play a role in biofilm formation through regulation of exopolysaccharide synthesis.

Protective efficacy as a function of persistence has been previously evaluated by this laboratory(25). The construction and characterization of multiple deletion mutants in *Brucella abortus* and *Brucella melitensis* has led to the conclusion that a vaccine candidate needs to persist in the host long enough in order to mount a strong protective immune response(15, 25). This observation is apparent here as well with the *B. melitensis* mucR mutant. Interestingly, the mucR mutant persists at least for 12 weeks in mice, similarly to the wild-type 16M, but the degree of colonization is significantly reduced compared to the parental strain during the acute phase of the infection. This difference in colonization properties may explain the lack of gross and microscopic changes associated with infection. Lack of hepatic granuloma formation, hepatomegaly or splenomegaly associated with vaccination suggests that immunization with the mutant is safe, and therefore superior to many other *Brucella* vaccines, including licensed ones. Most importantly, protection against the most common microscopic changes associated with the disease in mice such as granulomatous hepatitis, granulomatous splenitis or splenomegaly was not observed, indicating that vaccination with the mucR mutant not only reduced the bacterial burden in multiple organs but also prevents against the development of *Brucella*-associated pathologic changes. Lack of splenomegaly associated with vaccination has been previously demonstrated as a safety parameter in other vaccine candidates (2).

Protection against intraperitoneal challenge, observing the output of bacterial colonization in the spleen of mice, has been historically used as a means of evaluating *Brucella* vaccine efficacy (6, 27, 34, 39). Although this vaccination or challenge location does not reflect a natural route of infection, it has been extremely useful in determining the potential efficacy of vaccine candidates against brucellosis. Most importantly, it provides a reproducible and invariable means of comparing multiple vaccine candidate strains that had been studied for the past 30 to 50 years. When 16MΔmucR vaccinated mice were challenged against wild-type *Brucella melitensis* 16M, all animals demonstrated a statistically significant reduction in the bacterial burden in the spleen, lung and liver regardless of the vaccination dose. The marked reduction in bacterial burden in the spleen conferred by the mutant is impressive and comparable to other live attenuated vaccine candidates tested by this laboratory and others(2, 20, 21, 25). Although an intraperitoneal challenge is of historical importance, a more logical approach is the use of an aerosol challenge route, not only because of the documented evidence of aerosol transmission of these organisms, but also because of the potential threat of the use of *Brucella* as a bioterrorism agent(13, 18, 22, 26). It has been documented that 10 to 100 organisms are enough to cause disease in humans, and *Brucella* is therefore considered highly infectious when delivered by this route (7). Previous investigations performed by this laboratory has determined that BALB/c mice receiving an infectious dose of 5×109 CFU/ml added to the chamber nebulizer inhaled an average of 12,250 organisms per mouse (4.10 logs) and that tissue colonization reached a peak by 4 weeks post-exposure(23). The high dose (100-fold more bacteria that actually needed to establish an infection) and the time post-vaccination chosen to test efficacy, provide us the means to evaluate the vaccine candidate efficacy at the most stringent conditions. Interestingly and importantly, the bacterial burden in the spleen, liver and lung were markedly reduced in animals that received the vaccine, demonstrating the vaccine efficacy against an aerosol exposure. Gross and microscopic evaluation confirmed the protection against the pathologic changes associated with the disease. As expected, the highest number of bacterial were isolated from the lung. It is possible that a diminished inflammatory response in the lungs masks the efficacy in reducing the bacterial colonization, and although high bacterial counts were observed there were no significant gross or microscopic changes associated with the infection apart from an increased amount of BALT associated lymphoid tissue.

In the present invention, the intraperitoneal vaccination with the live attenuated vaccine candidate 16MΔmucR was able to markedly enhance the bacterial clearance in the spleen, lung and liver using two different challenge routes. Most importantly, vaccination conferred protection against *Brucella*-associated pathologic changes.

It is contemplated that any embodiment discussed in this specification can be implemented with respect to any method, kit, reagent, or composition of the invention, and vice versa. Furthermore, compositions of the invention can be used to achieve methods of the invention.

It may be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it may be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Application Publication No. 20110177127: *Brucella abortus* Proteins and Methods of Use Thereof U.S. Pat. No. 7,541,447: Process for the Preparation of an Improved *Brucella* Strain Plasmid to Develop the Strain and the Vaccine Comprising the Said Strain.

1. Allen, C. A., L. G. Adams, and T. A. Ficht. 1998. Transposon-derived *Brucella abortus* rough mutants are attenuated and exhibit reduced intracellular survival. Infection and immunity 66:1008-1016.

2. Arenas-Gamboa, A. M., T. A. Ficht, M. M. Kahl-McDonagh, G. Gomez, and A. C. Rice-Ficht. 2009. The *Brucella abortus* S19 DeltavjbR live vaccine candidate is safer than S19 and confers protection against wild-type challenge in BALB/c mice when delivered in a sustained-release vehicle. Infection and immunity 77:877-884.

3. Ashford, D. A., J. di Pietra, J. Lingappa, C. Woods, H. Noll, B. Neville, R. Weyant, S. L. Bragg, R. A. Spiegel, J. Tappero, and B. A. Perkins. 2004. Adverse events in humans associated with accidental exposure to the livestock brucellosis vaccine RB51. Vaccine 22:3435-3439.

4. Bahlawane, C., B. Baumgarth, J. Serrania, S. Ruberg, and A. Becker. 2008. Fine-tuning of galactoglucan biosynthesis in *Sinorhizobium* meliloti by differential WggR (ExpG)-, PhoB-, and MucR-dependent regulation of two promoters. J Bacteriol 190:3456-3466.

5. Bahlawane, C., M. McIntosh, E. Krol, and A. Becker. 2008. *Sinorhizobium* meliloti regulator MucR couples exopolysaccharide synthesis and motility. Mol Plant Microbe Interact 21:1498-1509.

6. Bosseray, N., and M. Plommet. 1990. *Brucella suis* S2, *Brucella melitensis* Rev. 1 and *Brucella abortus* S19 living vaccines: residual virulence and immunity induced against three *Brucella* species challenge strains in mice. Vaccine 8:462-468.

7. Bossi, P., A. Tegnell, A. Baka, F. Van Loock, J. Hendriks, A. Werner, H. Maidhof, and G. Gouvras. 2004. Bichat guidelines for the clinical management of brucellosis and bioterrorism-related brucellosis. Euro Surveill 9:E15-16.

8. Cassataro, J., C. A. Velikovsky, S. de la Barrera, S. M. Estein, L. Bruno, R. Bowden, K. A. Pasquevich, C. A. Fossati, and G. H. Giambartolomei. 2005. A DNA vaccine coding for the *Brucella* outer membrane protein 31 confers protection against *B. melitensis* and *B. ovis* infection by eliciting a specific cytotoxic response. Infection and immunity 73:6537-6546.

9. Cassataro, J., C. A. Velikovsky, G. H. Giambartolomei, S. Estein, L. Bruno, A. Cloeckaert, R. A. Bowden, M. Spitz, and C. A. Fossati. 2002. Immunogenicity of the *Brucella melitensis* recombinant ribosome recycling factor-homologous protein and its cDNA. Vaccine 20:1660-1669.

10. Cespedes, S., E. Andrews, H. Folch, and A. Onate. 2000. Identification and partial characterisation of a new protective antigen of *Brucella abortus*. Journal of medical microbiology 49:165-170.

11. Costerton, J. W. 1995. Overview of microbial biofilms. Journal of industrial microbiology 15:137-140.

12. Costerton, J. W., Z. Lewandowski, D. E. Caldwell, D. R. Korber, and H. M. Lappin-Scott. 1995. Microbial biofilms. Annual review of microbiology 49:711-745.

13. Davos, D. E., C. F. Cargill, M. R. Kyrkou, J. A. Jamieson, and G. E. Rich. 1981. Outbreak of brucellosis at a South-Australian abattoir. 2. Epidemiological investigations. The Medical journal of Australia 2:657-660.

14. Delpino, M. V., S. M. Estein, C. A. Fossati, P. C. Baldi, and J. Cassataro. 2007. Vaccination with *Brucella* recombinant DnaK and SurA proteins induces protection against *Brucella abortus* infection in BALB/c mice. Vaccine 25:6721-6729.

15. Ficht, T. A., M. M. Kahl-McDonagh, A. M. Arenas-Gamboa, and A. C. Rice-Ficht. 2009. Brucellosis: the case for live, attenuated vaccines. Vaccine 27 Suppl 4:D40-43.

16. Ficht, T. A., J. Pei, and M. Kahl-McDonagh. 2010. In vitro mutagenesis of *Brucella* species. Methods in molecular biology (Clifton, N.J. 634:15-35.

17. Godefroid, M., M. V. Svensson, P. Cambier, S. Uzureau, A. Mirabella, X. De Bolle, P. Van Cutsem, G. Widmalm, and J. J. Letesson. *Brucella melitensis* 16M produces a mannan and other extracellular matrix components typical of a biofilm. FEMS Immunol Med Microbiol 59:364-377.

18. Guihot, A., P. Bossi, and F. Bricaire. 2004. [Bioterrorism with brucellosis]. Presse Med 33:119-122.

19. Hay, I. D., U. Remminghorst, and B. H. Rehm. 2009. MucR, a novel membrane-associated regulator of alginate biosynthesis in *Pseudomonas aeruginosa*. Applied and environmental microbiology 75:1110-1120.

20. Hong, P. 2005. Dissertation. Texas A&M University, College Station.

21. Hong, P. C., R. M. Tsolis, and T. A. Ficht. 2000. Identification of genes required for chronic persistence of *Brucella abortus* in mice. Infection and immunity 68:4102-4107.

22. Jamieson, J. A., G. E. Rich, M. R. Kyrkou, C. F. Cargill, and D. E. Davos. 1981. Outbreak of brucellosis at a South-Australian abattoir. 1. Clinical and serological findings. The Medical journal of Australia 2:593-596.

23. Kahl-McDonagh, M. M., A. M. Arenas-Gamboa, and T. A. Ficht. 2007. Aerosol infection of BALB/c mice with *Brucella melitensis* and *Brucella abortus* and protective efficacy against aerosol challenge. Infection and immunity 75:4923-4932.

24. Kahl-McDonagh, M. M., P. H. Elzer, S. D. Hagius, J. V. Walker, Q. L. Perry, C. M. Seabury, A. B. den Hartigh, R. M. Tsolis, L. G. Adams, D. S. Davis, and T. A. Ficht. 2006. Evaluation of novel *Brucella melitensis* unmarked deletion mutants for safety and efficacy in the goat model of brucellosis. Vaccine 24:5169-5177.

25. Kahl-McDonagh, M. M., and T. A. Ficht. 2006. Evaluation of protection afforded by *Brucella abortus* and *Brucella melitensis* unmarked deletion mutants exhibiting different rates of clearance in BALB/c mice. Infection and immunity 74:4048-4057.

26. Miller, C. D., J. R. Songer, and J. F. Sullivan. 1987. A twenty-five year review of laboratory-acquired human infections at the National Animal Disease Center. Am Ind Hyg Assoc J 48:271-275.

27. Montaraz, J. A., and A. J. Winter. 1986. Comparison of living and nonliving vaccines for *Brucella abortus* in BALB/c mice. Infection and immunity 53:245-251.

28. Mueller, K., and J. E. Gonzalez. Complex regulation of symbiotic functions is coordinated by MucR and quorum sensing in *Sinorhizobium* meliloti. J Bacteriol 193:485-496.

29. Nicoletti, P. 1990. Vaccination against *Brucella*. Advances in biotechnological processes 13:147-168.

30. Onate, A. A., S. Cespedes, A. Cabrera, R. Rivers; A. Gonzalez, C. Munoz, H. Folch, and E. Andrews. 2003. A DNA vaccine encoding Cu,Zn superoxide dismutase of *Brucella abortus* induces protective immunity in BALB/c mice. Infection and immunity 71:4857-4861.

31. Pappas, G., N. Akritidis, M. Bosilkovski, and E. Tsianos. 2005. Brucellosis. The New England journal of medicine 352:2325-2336.

32. Pasquevich, K. A., S. M. Estein, C. Garcia Samartino, A. Zwerdling, L. M. Coria, P. Barrionuevo, C. A. Fossati, G.

H. Giambartolomei, and J. Cassataro. 2009. Immunization with recombinant *Brucella* species outer membrane protein Omp16 or Omp19 in adjuvant induces specific CD4+ and CD8+ T cells as well as systemic and oral protection against *Brucella abortus* infection. Infection and immunity 77:436-445.

33. Perkins, S. D., S. J. Smither, and H. S. Atkins. Towards a *Brucella* vaccine for humans. FEMS microbiology reviews.

34. Plommet, M., and N. Bosseray. 1977. [Checking of anti-*Brucella* vaccines by counting the *Brucella* in the spleen of intraperitoneally innoculated, vaccinated or unvaccinated, mice]. Journal of biological standardization 5:261-274.

35. Rinaudi, L. V., F. Sorroche, A. Zorreguieta, and W. Giordano. Analysis of the mucR gene regulating biosynthesis of exopolysaccharides: implications for biofilm formation in *Sinorhizobium meliloti* Rm1021. FEMS microbiology letters 302:15-21.

36. Saez, D., I. Guzman, E. Andrews, A. Cabrera, and A. Onate. 2008. Evaluation of *Brucella abortus* DNA and RNA vaccines expressing Cu—Zn superoxide dismutase (SOD) gene in cattle. Vet Microbiol 129:396-403.

37. Schurig, G. G., N. Sriranganathan, and M. J. Corbel. 2002. Brucellosis vaccines: past, present and future. Vet Microbiol 90:479-496.

38. Spink, W. W., J. W. Hall, 3rd, J. Finstad, and E. Mallet. 1962. Immunization with viable *Brucella* organisms. Results of a safety test in humans. Bull World Health Organ 26:409-419.

39. Winter, A. J., G. G. Schurig, S. M. Boyle, N. Sriranganathan, J. S. Bevins, F. M. Enright, P. H. Elzer, and J. D. Kopec. 1996. Protection of BALB/c mice against homologous and heterologous species of *Brucella* by rough strain vaccines derived from *Brucella melitensis* and *Brucella suis* biovar 4. American journal of veterinary research 57:677-683.

40. Wu, Q., J. Pei, C. Turse, and T. A. Ficht. 2006. Mariner mutagenesis of *Brucella melitensis* reveals genes with previously uncharacterized roles in virulence and survival. BMC Microbiol 6:102.

41. Kahl-McDonagh, M. M., and T. A. Ficht. 2006 Evaluation of protection afforded by *Brucella abortus* and *Brucella melitensis* unmarked deletion mutants exhibiting different rates of clearance in BALB/c mice. Infection & Immunity. 74(7):4048-57.

What is claimed is:

1. A vaccine composition comprising:

a *Brucella melitensis* comprising one or more attenuating gene knockouts and further comprising a diagnostic gene knockout; and an encapsulating agent comprising vitelline protein B capable of releasing the *Brucella melitensis* at a predetermined rate, wherein the vaccine is free of side effects.

2. The vaccine composition of claim 1, wherein the composition further comprises an adjuvant or a pharmaceutically acceptable carrier.

3. The vaccine composition of claim 1, wherein the encapsulating agent is an alginate bead or a microsphere.

4. The vaccine composition of claim 1, wherein the attenuating gene knockout is ΔvjbR.

5. The vaccine composition of claim 1, wherein said diagnostic gene knockout comprises a differentiation of infected animals from vaccinated animals (DIVA) mutant is ΔvirB 12.

6. The vaccine composition of claim 1, wherein the vaccine further comprises a marker for serological testing, wherein the marker is DIVA mutant is ΔvirB12.

7. The vaccine composition of claim 1, wherein the vaccine comprises ΔvjbR/DIVA.

8. The vaccine composition of claim 1, wherein the strain is a double mutant and further comprises a third mutation, wherein the third mutation is a marker for serological testing.

9. The vaccine composition of claim 8, wherein the double mutant is a ΔvirB2/ΔvjbR mutant.

10. The vaccine composition of claim 8, wherein the third mutation is DIVA mutant comprising ΔvirB12.

11. The vaccine composition of claim 1, wherein the strain comprises a ΔvirB2/ΔvjbR/DIVA mutant.

12. The vaccine composition of claim 1, further comprising one or more optional antibiotic markers, wherein the antibiotic marker is Kanamycin.

13. The vaccine composition of claim 1, wherein the vaccine is capable of prophylaxis, amelioration of symptoms, treatment, or any combinations thereof against brucellosis in a human or an animal subject.

14. The vaccine composition of claim 1, wherein the vaccine is adapted for an oral, an intranasal, a parenteral, an intradermal, an intramuscular, an intraperitoneal, an intravenous, a subcutaneous, an epidural, a mucosal, a rectal, a vaginal, a sublingual, or a buccal administration.

15. A vaccine composition comprising:

a single or a double mutant strain of *Brucella melitensis* comprising one or more attenuating gene knockouts and further comprising a diagnostic gene knockout, wherein the attenuating gene knockouts comprise, ΔvjbR, wherein the diagnostic gene knockout comprises a differentiation of infected animals from vaccinated animals (DIVA) mutant that includes ΔvirB12; and an encapsulating agent comprising vitelline protein B capable of releasing the *Brucella melitensis* at a predetermined rate, wherein the vaccine is free of side effects.

16. The vaccine composition of claim 15, wherein the composition further comprises an adjuvant or a pharmaceutically acceptable carrier.

17. The vaccine composition of claim 15, further comprising one or more optional antibiotic markers, wherein the antibiotic marker is Kanamycin.

18. The vaccine composition of claim 15, wherein the vaccine is capable of prophylaxis, amelioration of symptoms, treatment, or any combinations thereof against brucellosis in a human or an animal subject.

19. The vaccine composition of claim 15, wherein the vaccine is adapted for an oral, an intranasal, a parenteral, an intradermal, an intramuscular, an intraperitoneal, an intravenous, a subcutaneous, an epidural, a mucosal, a rectal, a vaginal, a sublingual, or a buccal administration.

20. A vaccine composition comprising:

a single or double mutant strain of *Brucella melitensis* comprising:

one or more attenuating gene knockouts and further comprising a diagnostic gene knockout, wherein the attenuating gene knockouts comprise ΔvjbR; and a marker for serological testing, wherein the marker is used for differentiation of infected animals from vaccinated animals (DIVA) mutant comprising ΔvirB12; and an encapsulating agent comprising vitelline protein B capable of releasing the strain at a predetermined rate, wherein the vaccine is free of side effects.

21. The vaccine composition of claim 20, wherein the composition further comprises an adjuvant or a pharmaceutically acceptable carrier.

22. The vaccine composition of claim 20, further comprising one or more optional antibiotic markers, wherein the antibiotic marker is Kanamycin.

23. The vaccine composition of claim 20, wherein the vaccine is capable of prophylaxis, amelioration of symptoms, treatment, or any combinations thereof against brucellosis in a human or an animal subject.

24. The vaccine composition of claim 20, wherein the vaccine is adapted for an oral, an intranasal, a parenteral, an intradermal, an intramuscular, an intraperitoneal, an intravenous, a subcutaneous, an epidural, a mucosal, a rectal, a vaginal, a sublingual, or a buccal administration.

* * * * *

SEQUENCE LISTING

```
<160> NUMBER OF SEQ ID NOS: 16

<210> SEQ ID NO 1
<211> LENGTH: 29
<212> TYPE: DNA
<213> ORGANISM: Artificial sequence
<220> FEATURE:
<223> OTHER INFORMATION: Synthetic oligonucleotide.

<400> SEQUENCE: 1

ggaattcggc aaagcgagtg ggtgattag                                         29


<210> SEQ ID NO 2
<211> LENGTH: 28
<212> TYPE: DNA
<213> ORGANISM: Artificial sequence
<220> FEATURE:
<223> OTHER INFORMATION: Synthetic oligonucleotide.

<400> SEQUENCE: 2

cgggatcctg agcaagtgcg ggaatagc                                          28


<210> SEQ ID NO 3
<211> LENGTH: 28
<212> TYPE: DNA
<213> ORGANISM: Artificial sequence
<220> FEATURE:
<223> OTHER INFORMATION: Synthetic oligonucleotide.

<400> SEQUENCE: 3

cgggatcctg ggaatggagc ggctttag                                          28


<210> SEQ ID NO 4
<211> LENGTH: 29
<212> TYPE: DNA
<213> ORGANISM: Artificial sequence
<220> FEATURE:
<223> OTHER INFORMATION: Syntehtic oligonucleotide.

<400> SEQUENCE: 4

gctctagatt tgaacacttg gcgatagcg                                         29
```

-continued

<210> SEQ ID NO 5
<211> LENGTH: 33
<212> TYPE: DNA
<213> ORGANISM: Artificial sequence
<220> FEATURE:
<223> OTHER INFORMATION: Synthetic oligonucleotide.

<400> SEQUENCE: 5
cgggatcccg cacgtcttga gcgattgtgt agg 33

<210> SEQ ID NO 6
<211> LENGTH: 33
<212> TYPE: DNA
<213> ORGANISM: Artificial sequence
<220> FEATURE:
<223> OTHER INFORMATION: Synthetic oligonucleotide.

<400> SEQUENCE: 6
cgggatcccg ggacaacaag ccagggatgt aac 33

<210> SEQ ID NO 7
<211> LENGTH: 28
<212> TYPE: DNA
<213> ORGANISM: Artificial sequence
<220> FEATURE:
<223> OTHER INFORMATION: Synthetic oligonucleotide.

<400> SEQUENCE: 7
cgggatccct ggaggaaaac aatctggg 28

<210> SEQ ID NO 8
<211> LENGTH: 31
<212> TYPE: DNA
<213> ORGANISM: Artificial sequence
<220> FEATURE:
<223> OTHER INFORMATION: Synthetic oligonucleotide.

<400> SEQUENCE: 8
aagacggcgc gcccgaacct gtatctgcct g 31

<210> SEQ ID NO 9
<211> LENGTH: 37
<212> TYPE: DNA
<213> ORGANISM: Artificial sequence
<220> FEATURE:
<223> OTHER INFORMATION: Syntehtic oligonucleotide.

<400> SEQUENCE: 9
gttcgggcgc gccgtcttaa cccaaaaccg cttcgta 37

<210> SEQ ID NO 10
<211> LENGTH: 32
<212> TYPE: DNA
<213> ORGANISM: Artificial sequence
<220> FEATURE:
<223> OTHER INFORMATION: Synthetic oligonucleotide.

<400> SEQUENCE: 10
gctctagagg gttttctgat cgatctggta gc 32

<210> SEQ ID NO 11
<211> LENGTH: 30
<212> TYPE: DNA
<213> ORGANISM: Artificial sequence
<220> FEATURE:
<223> OTHER INFORMATION: Syntehtic oligonucleotide.

```
<400> SEQUENCE: 11

ggcgcgccac gtcttgagcg attgtgtagg                                         30


<210> SEQ ID NO 12
<211> LENGTH: 31
<212> TYPE: DNA
<213> ORGANISM: Artificial sequence
<220> FEATURE:
<223> OTHER INFORMATION: Syntehtic oligonucleotide.

<400> SEQUENCE: 12

ggcgcgccgg acaacaagcc agggatgtaa c                                       31


<210> SEQ ID NO 13
<211> LENGTH: 32
<212> TYPE: DNA
<213> ORGANISM: Artificial sequence
<220> FEATURE:
<223> OTHER INFORMATION: Synthetic oligonucleotide.

<400> SEQUENCE: 13

gctctagagc ccatcaacaa caggacaaac gg                                      32


<210> SEQ ID NO 14
<211> LENGTH: 32
<212> TYPE: DNA
<213> ORGANISM: Artificial sequence
<220> FEATURE:
<223> OTHER INFORMATION: Syntehtic oligonucleotide.

<400> SEQUENCE: 14

ggcggcgcgc ctggttgctc cgaactatgc tg                                      32


<210> SEQ ID NO 15
<211> LENGTH: 32
<212> TYPE: DNA
<213> ORGANISM: Artificial sequence
<220> FEATURE:
<223> OTHER INFORMATION: Synthetic oligonucleotide.

<400> SEQUENCE: 15

ccaggcgcgc cgccgctgcg tatttcataa tc                                      32


<210> SEQ ID NO 16
<211> LENGTH: 33
<212> TYPE: DNA
<213> ORGANISM: Artificial sequence
<220> FEATURE:
<223> OTHER INFORMATION: Syntehtic oligonucleotide.

<400> SEQUENCE: 16

gctctagagc ctttgcaggt tttccgtatc ttt                                     33
```